United States Patent [19]
Brechot et al.

[11] Patent Number: 5,866,139
[45] Date of Patent: Feb. 2, 1999

US005866139A

[54] NUCLEOTIDE AND PEPTIDE SEQUENCES OF A HEPATITIS C VIRUS ISOLATE, DIAGNOSTIC AND THERAPEUTIC APPLICATIONS

[75] Inventors: Christian Brechot; Dina Kremsdorf, both of Paris; Colette Porchon, Gentilly, all of France

[73] Assignee: Institut Pasteur, Paris, France

[21] Appl. No.: 483,695

[22] Filed: Jun. 7, 1995

Related U.S. Application Data

[62] Division of Ser. No. 965,285, Mar. 18, 1993.

[51] Int. Cl.[6] .......................... A61K 38/04; A61K 39/29
[52] U.S. Cl. ..................... 424/228.1; 424/184.1; 424/185.1; 424/278.1; 530/324; 530/328; 530/329; 530/350; 530/812
[58] Field of Search ..................... 530/324, 325, 530/326, 327, 328, 329, 350, 810, 811, 820, 826; 424/184.1, 185.1, 228.1, 278.1

[56] References Cited

FOREIGN PATENT DOCUMENTS

| | | |
|---|---|---|
| 0 318 216 | 5/1989 | European Pat. Off. . |
| 0 398 748 | 11/1990 | European Pat. Off. . |
| WO 89/04669 | 6/1989 | WIPO . |
| WO 90/00597 | 1/1990 | WIPO . |
| WO 90/11089 | 10/1990 | WIPO . |
| WO 92/21759 | 12/1992 | WIPO . |

OTHER PUBLICATIONS

Okamoto et al., The 5′–Terminal Sequence of the Hepatitis C Virus Genome, Japan J. Exp. Med. 60(3):167–177 (1990).
Weiner et al., Variable and Hypervariable Domains Are Found in the Regions of HCV Corresponding to the Flavivirus Envelope and NS1 Proteins and the Pestivirus Envelope Glycoproteins, Virology 180: 842–848 (1991).
Choo et al., Isolation of a cDNA Clone Derived from a Blood–Borne Non–A, Non–B Viral Hepatitis Genome, Science 244:359–362 (1989).

*Primary Examiner*—Laurie Scheiner
*Attorney, Agent, or Firm*—Finnegan, Henderson, Farabow, Garrett & Dunner, L.L.P.

[57] ABSTRACT

This invention relates to purified HCV E1 peptides, immunogenic composition comprising purified HCV E1 peptides, and a diagnostic kit for detecting HCV E1-specific antibodies. The purified HCV E1 peptide has an amino acid selected from the group consisting of SEQ ID NO:3; SEQ ID NO:5; and SEQ ID NO:7.

21 Claims, 19 Drawing Sheets

FIG. 2

```
1  TTCTGGAAGACGGGCGTGAACTATGCAACAGGGAACCTTCCTGGTTGCTCTTTCTCTATCC  60
2  ............................................................  60
3  .........G..........................TT.G..C.................  60
4  ............................................................  60
5  .........G..........................T.G..C................T  60

1  TCCTCCTGGCCCTGCTCTCTTGCCCTGACTGTGCCCGGTCAGCCTACCAAGTACGCAATT  120
2  ...T.............................T..........T.G............  120
3  ....T......T..G..C..TT.....CA.C..A..T..C..T..TG.........CG  120
4  ....T.........................T..........C.................  120
5  ....T......TT..G..C..TT.....CA.C..A..T..C..T..TG.........CG  120

1  CTCGCGGCCTTTACCATGTCACCAATGATTGCCCTAACTCGAGTATTGTGTACGAGACGG  180
2  .CACG..G.........C.............................G...........  180
3  TGTC...GA.A........A.C..C...T.C......A.C.......T...G........  180
4  .CACA..G.....T..................G.C..C..T.C...........G..C..  180
5  TGTC...GA.A.............G.C..C..T.C......A.C.......T...G.A..  180

1  CCGATAGCATTCTACACTCTCCGGGGTGTGTCCCTTGCGTTCGCGAGGGTAACACCTCGA  240
2  ...GC..C..G..A.............C.................T..C..G........  240
3  .G..CGTG..CA.G..TG.C..C.......C.G..C.........G...AAC..TT....CC  240
4  A....GC...C..G..TA.....................C...GT........  240
5  .G..C.TG..CA.G..TA.....C................G...AC.........G...CC  240
```

*FIG. 3A*

```
1  AATGTTGGGTGGCGGTGGCCCCCTACAGTGCGCCACCAGAGACGGCAGACTCCCCACAACGC  300
2  GG...........A..A.......G..G.......G.T.A.........G.G.........  300
3  GT..C....A...C.CA.T..C..GC...GG....GA.T.C...CG......T...A....  300
4  GG...........A..A....C..G..A.......G...A.........G.G.........  300
5  GT..C....A...C.CA.T..C..GC...GG....GA.T.C...CG......T...A....  300

1  AGCTTCGACGTCATATCGATCTGCTCGTCGGGAGCGCCACCCCTCTGCTCGGCCCTCTATG  360
2  ...............C..................T.........................  360
3  CAT.A.....C..CG.......CT........T....CG..TG.TT......C..TA.G..C.  360
4  ....C.....C..CG.......T.........T............................  360
5  CAA.A.....C..CG.......CT........T....GCG..TG.TT......C..TA.G..C.  360

1  TGGGGGACTTGTGCGGGTCCGTCTTCCCTCGTCGGTCAATTGTTCACCTTCTCCCCAGGC  420
2  .......C.A..........T.....T....T.......C....................  420
3  .......TC.C......A..T..T......A..TCC..GC.........G..TC.C....  420
4  .......TC...........T.........TA.T....C...T.................  420
5  .......TC.C......A..T..T......TCC..GC.........G..TC.C....    420

1  GCCACTGGACAAACGCAAGAACTGCAACTGTTCCATCTACCCCGGCCACGTAACGGGTCACC  480
2  .............G........GT....T..C..T.....T........TA..........  480
3  ..G..TGA......GTA...G.......C..A....T.........T..T.A..C..T..  480
4  ......................G........T.....T.........TA.........T.  480
5  ..G..TGA......GT....G..............T...........TT..T.A......  480
```

*FIG. 3B*

| | | |
|---|---|---|
| 1 | GCATGGCATGGGATATGATGA | 501 |
| 2 | .................... | 501 |
| 3 | .....T.............. | 501 |
| 4 | .................... | 501 |
| 5 | ......T............. | 501 |

FIG. 3C

```
1  LEDGVNYATGNLPGCSFSILLLALLSCLTVPASAYQVRNSRGLYHVTNDCPNSSIVYETA   60
2  .................F..............T......I.E...VS.I.........A.  60
3  .................F...................T.........S..........A.  60
4  .................F......................I.E...VS.I........AH  60
5  .................F...................T.........S..........A.  60

1  DSILHSPGCVPCVREGNTSKCWVAVAPTVATRDGRLPTTQLRRHIDLLVGSATLCSALYV   120
2  ...A..T......A.R......MT........A.......T.....V............   120
3  .V.M.A.......N.S.R....LT.L.A.NASV.....T..V.......T.AF....M.   120
4  ...A..T......V.R......MT........A......TI...V..............   120
5  .M.M.T.......D.S.R....LT.L.A.NASV.........V......A..AF...M.   120

1  GDLCGSVFLVGQLFTFSPRRHWTTQDCNCSIYPGHVTGHRMAWDMM                 166
2  ..............IS..........G......I............                166
3  ..............I.........E.V......S.............               166
4  ...............S.........G......I.............                166
5  ..............S.........E.V.....LS.............               166
```

FIG. 4

```
    AATGGCTCAACTGCTCAGGGTCCCGCAAGCCATCTTGGACATGATCGCTGGTGCCCACTG   60
1   ......G.......C..A...A..........................T...........   60
2   ......G......C.CA....A......................................   60
3   GG..T.G....GT..........A....TG..G............G.G..G.G........   60
4   GG..T.G..GT.A..C..A....A....TG..A............G.G..G.G........   60
5                                                                  60

GGGAGTCCTAGCGGGCATAGCGTATTTCTCCATGGTGGGGAACTGGGCGAAGGTCCTGCT  120
1   ......G.....................................................  120
2   ......G.................................................G..  120
3   ......G......C.T..C..C.AT...........A...................G..  120
4   ......G......C.T..C..C.AT...................T.........T..A.  120
5                                             T...TT..A.          120

AGTGCTGTTGCTGTTCGCCCGGCGTCGATGCGGAAACCTACACCACCGGGGGAGTACTGC  180
1   ...C..A..T.................C...........C..GT.....A..G.C.G..  180
2   ...........T.............................AT.GT.T....ACAAG.C.  180
3   T...GC.C.A..C...........T..C.G..G......GT.G......GCGG..CAG.  180
4   T..A..C.A..C..T.........T..C.G.C.T......CG.GTG..G....GTGCAA.G 180
5                                                                  180

CAGGACCACGCAAGGACTCGTCAGCCTTTTCAGTGCGAGGCGCCAAGCAGGACATCCAGCT 240
1   .CAC..TGT..TCT..T.T..T...CC..GCA.C.............A..G.........  240
2   .C.CG...T.TCT...T..T..T..C....CA.C.........T...A............  240
3   .CAC....CTCCACG...CGTC.....C....TCA.CT..G..GTCT..AGA........  240
4   .CACGT...CTCTAC...ACGTC....C..T.A.CT..G..GTCC....A.A..T.....  240
5                                                                  240
```

*FIG. 5A*

```
1  GATCAACACCAACGGCAGCTGGCACACATTAATCGCACAGCTTTGAACTGTAATGAGAGCCT  300
2  .............T........................C..G..CC.....T........  300
3  .............T........................C..A..C......A........  300
4  TG.G..T...............................C..CA.G..T..CC.A...CTC...  300
5  TG.A..........T.......T......T..C.....CA.G..T..CC......CTC...  300

1  CGACACCGGCTGGGTAGCGGGGCTCTTCTATTACCACAAATTCAACTCTTCAGGCTGCCC  360
2  TA.......T.G..A......T.....C.....G................T......  360
3  TA.......T.G..A......TA.....C.A...................T......  360
4  .C.....T.G.TCC.T..C.C...G.......CACA.....GG........G..C..G.  360
5  .C.A..T.G.TCC.T..C.C...G.................................  325

1  CGAGAGGATGGCCAGCTGCAGACCCCTTGCCGATTTCGACCAGGGCTGGGGCCCTATCAG  420
2  T....C.A..............C.....A......T.......................  420
3  ......T..............C...G...A.....T.......................  420
4  G......C.C.............C.C....A...A.TGG....C......A........C  420
5  ..........................................................  325

1  TTATGCCAACGGAACCGGCCCTGAACACCGCCCCTACTGCTGGCACTACCCCCCAAAGCC  480
2  ..............G......C..C..G..............................A..  480
3  .C............G......C..C..A.......T..T....................  480
4  C...A.TG.GCCTGA.A.....G..T..GA.G..T..T............T...G.G..TCGA..  480
5  ..........................................................  325
```

FIG.5B

```
1  TTGTGGTATCGTGTGCCAGCACAGACCGTATGTGGCCCAGTGTATTGCTTCACTCCTAGCCC    540
2  ...C.....T......C..GA...GT..G......T..G..A..................    540
3  ...C.....................C...A...G..........G..A............    540
4  G............................A..C..GTC..CAG..G......T.......    540
5  .............................................................C..A....  325

1  CGTGGTGGTGGGGACGACCAATAAGTTGGGGCGCACCCACTTACAACTGGGGTTGTAATGA    600
2  ...............A..........G..C..G......G..........GAA.......    600
3  ............................G.C.G..C........................    541
4  ..T..........................................................    541
5  .............................................................  325

1  TACGGACGTCTTCGTCCTTAATAACACCAGGCCACCGCTGGGCAATTGGTTCGGCTGCAC    660
2  ............................C...T...........................T..T..    660
3  .............................................................    541
4  .............................................................    541
5  .............................................................  325

1  CTGGGTGAACTCATCTGGATTTACTAAAGTGTGCCGAGCGCCTCCCTGTGTCATCGGAGG    720
2  ..A.............A.........C..C...............................    720
3  ..............................T..............................    541
4  .............................................................    541
5  .............................................................  325
```

FIG. 5C

```
1   AGCGGGCAATAACACCCTTGTACTGCCCCACTGACTGTTTCCGCAAGCATCCGGAAGCTAC       780
2   G..................C.....C.............T..C.................       780
3   ............................................................       541
4   ............................................................       541
5   ............................................................       325

1   ATACTCCCGATGTGGCTCCGGTCCTTGGATCACGCCCCAGGTGCCTGGTTGGCTATCCTTA       840
2   .....T..G..C....................C...........C.A....C..G.....       840
3   ............................................................       541
4   ............................................................       541
5   ............................................................       325

1   TAGGCTCTGGCATTATCCCTGTACTGTCAACTACACCCCTGTTCAAGGTCAGGATGTACGT       900
2   .T...............T....CA...........A.A..T..AA...............       900
3   ............................................................       541
4   ............................................................       541
5   ............................................................       325

1   GGGAGGGGTCGAGCACAGGCTGCAAGTCGCTTGCAACTGGAACGCGGGGCCGAGCGTTGTAA       960
2   .........A...........G...CT..C.....................A......CG.       960
3   ............................................................       541
4   ............................................................       541
5   ............................................................       325
```

FIG. 5D

```
1  TCTGGACGACAGGGACACAGGTCCGAGCTCAGTCCGCTGCTGTGTCTACCACACAGTGGCA   1020
2  .........A..................................................   1020
3  ............................C...T.A......A.C..T.............    541
4  ............................................................    541
5  ............................................................    325

1  GGTCCTCCCGTGTCCTTTACGACCTTGCCAGCCTTGACTACCGGCCTCATCCACCTCCA    1080
2  ............................................................   1080
3  .....................C.A...C.A........T.C...................    541
4  ............................................................    541
5  ............................................................    325

1  CCAGAACATCGTGGACGTGCAATATTTGTACGGGGTGGGTCAAGCATTGTGTCCTGGGC    1140
2  .........T.................G..C.............................   1140
3  ............................................C.C............    541
4  ............................................................    541
5  ............................................................    325

1  CATCAAGTGGGAGTACGTCATTCTCCCTGTTCTCCCTGCTTGCAGACGCGCGTCTGCTC    1200
2  ...T.................G......................................   1200
3  ..........................C..T..............................    541
4  ............................................................    541
5  ............................................................    325
```

```
1  CTGCTTGTGG........
2           ........
3           ........
4           ........
5           ........
```

FIG. 6A

```
1  AGNNTLYCPTDCFRKHPEATYSRCGSGPWITPRCLVGYPYRLWHYPCTVNYTLFKVRMYV    300
2  .........H..........D.................................         300
3  ......................................D..........I..I.         180
4  ...................................................I..I.       180
5  ........................................................       108

1  GGVEHRLQVACNWTRGERCNLDDRDRSELSPLLLSTTQWVLPCSFTTLPALTTGLIHLH    360
2  .......EA............D.E..............T...................    360
3  .........................................S...............    180
4  ..........................................................   180
5  ..........................................................   108

1  QNIVDVQYLYGVGSSIVSWAIKWEYVILLFLLLADARVCSCLW                    403
2  ...............A..........V...............                    180
3  ...........................................                   180
4  ...........................................                   180
5  ...........................................                   108
```

FIG. 6B

```
1  ACAATACGTGTGTCACCCAGACAGTCGACTTCAGCCTTGACCCTACCTTCACCATTGAAA    60
2  ...........................T...............................G..    60
3  GT..C..A......T...G......T.......T.G..T..C..TC........C..G.    60

1  CAACAACGCTTCCCCAGGATGCTGTCTCCCGCACTCAACGTCGGGGCAGGACTGGCAGGG   120
2  ...TC...C...................................................   120
3  .G..G..CG.G....A......G.T.G......G.T.G......G..G..A..T......   120

1  GGAAGCCAGGCATTTACAGATTTGTGGCACCTGGAGAGCCGCCCCTCCGGCATGTTCGACT   180
2  ..........................................G..G.............   180
3  .C.G.AG......C..T..G....A.T..A.....A..G......G.CG........T.   180

1  CGTCCCGTCCTCTCTGCGAGTGCTATGACGCAGGCTGTGTGCTTGGTATGAGCTCACGCCCGCCG   240
2  .............T..................T............................T.   240
3  .T..G.....A..T......T..........G..............................   240

1  AGACCACCAGTCAGGCTACGAGCATACATGAACACCCCGGGACTTCCCGTGTGCCAAGACC   300
2  ...T....T.................G.........G.................C....   300
3  ....T.G..T..T.G..T...C.A..T..A..A..GT.G....................   300
```

FIG. 8A

```
1  ATCTTGAGTTTTGGGAGGGCGTCTTCACGGGTCTCACCCATATAGACGCCCACTTCCTAT  360
2  .....A...............T.A..C......T........T..............    360
3  .....G.........A......A..C......C..............T.G.......   360

1  CCCAGACAAAGCAGAGTGGGGAAAAACCTTCCTTACCTGGTAGCGTACCAAGCCACCGTGT  420
2  ................G..................................A........ 420
3  ....T......GCA..A..C...T.C..C...........A...................  420

1  GCGCTAGGGCCCCAAGCCCCTCCCCGTCGTGGGACCAGATGTGGAAGTGCTTGATTCGTC  480
2  .......T..............A.................T.............C...  480
3  ....C...TA.G..T..A..T..A........T..A.........TC.C..A..G...  480

1  TCAAGCCCCACCCTCCATGGGCCAACACCCCTGCTATACCGACTGGGCGCTGTTCAGAATG  540
2  ...........................A................................ 540
3  .A....T..G.G..C.........G..........G..TA.G..A..A..C..C......  540

1  AAGTCACCCTGACGCACCCAATCACCAAATATATCATGACATGTCGGCTGACCTGG  600
2  ..A................G..............C........C...........  600
3  ..G..........C..A.....T..A.............................  569
```

FIG. 8B

```
1  AGGTCGTCACGAGTACCTGGGTGCTCGTGTGGGCGGCGTTCTGGCTGCTTTGGCCGGCGTATT    660
2  ..........................C.............T..........C...........    660
3  ...........................................................      569

1  GCCTATCCACAGGCTGCGTGGTCATAGTAGGCAGGGTCATTTGTCCGGGAAGCCGGCAA        720
2  ...G..A...............G................G.C.......                720
3  ...........................................................      569

1  TCATACCCGACAGGGAAGTCCTCTACCGGGAGTTCGATGAGATGGAAGAGTGCTCTCAGC       780
2  ............T..............A.....                                 780
3  ...........................................................      569

1  ACTTGCCATACATCGAGCAAGGGATGATGCTCGCCGAGCAGTTCAAGCAGAAGGCCCTCG       840
2  .....A..G....................                                     840
3  ...........................................................      569

1  GCCTCCCTGCAAACACGGTCCCCGCCAGGAGGTCATCACCCCTGCTGTCCAGACCAACT        900
2  .........G..CGC..........T..........T...G........                 900
3  ...........................................................      569

1  GGCAGAGACTCGAGGCCTTCTGGGCGAAGCATATGTGGAACTT                        943
2  ....A..A.......A...........                                       943
3  ...........................................................      569
```

*FIG. 8C*

```
1   NTCNVQTVDFSLDPTFTIETTLPQDAVSRTQRRGRTGRGKPGIYRFVAPGERPSGMFDS    60
2   ................I.........................................    60
3   ..........L.....V............RR........T......A...........    60

1   SVLCECYDAGCAWYELTPAETTVRLRAYMNTPGLPVCQDHLEFWEGVFTGLTHIDAHFLS   120
2   ...........................S..............................   120
3   .....................S.........L..........................   120

1   QTKQSGENLPYLVAYQATVCARAQAPPPSWDQMKCLIRLKPTLHGPTPLLYRLGAVQNE   180
2   ..........................................................   180
3   ....A.D.F................K................................   180

1   VTLTMPITKYIMTCMSADLEVVTSTWVLVGGVLAALAAYCLSTGCVVIVGRVILSGKPAI   240
2   I......V..................................V...............   240
3   ..........................................................   189

1   IPDREVLYREFDEMEECSQHLPYIEQGMMLAEQFKQKALGLLQTRSRQAEVITPAVQTNW   300
2   .............................................A............   300
3   .................................A...........A....E.......   189

1   QRLEAFWAKHMWN                                                313
2   .K..T........                                                313
3   .............                                                189
```

FIG. 9

NUCLEOTIDE AND PEPTIDE SEQUENCES OF A HEPATITIS C VIRUS ISOLATE, DIAGNOSTIC AND THERAPEUTIC APPLICATIONS

This is a division of application Ser. No. 07/965,285, filed Mar. 18, 1993.

The present invention relates to nucleotide and peptide sequences of a European, more particularly French, strain of the hepatitis C virus, as well as to the diagnostic and therapeutic applications of these sequences.

The hepatitis C virus is a major causative agent of infections by viruses previously called "Non-A Non-B" viruses. Infections by the C virus in fact now represent the most frequent forms of acute hepatitides and chronic Non-A Non-B hepatitides (Alter et al. (1), Choo et al., (3); Hopf et al., (5); Kuo et al., (8); Miyamura et al., (11). Furthermore, there is a relationship (the significance of which is still poorly understood) between the presence of anti-HCV antibodies and the development of primary liver cancers. It has also been shown that the hepatitis C virus is involved in both chronic or acute Non-A Non-B hepatitides linked to transfusions of blood products or of sporadic origin.

The genome of the hepatitis C virus has been cloned and the nucleotide sequence of an American isolate has been described in EP-A-0 318 216, EP-A-0 363 025, EP-A-0 388 232 and WO-A-90/14436. Moreover, data is currently available on the nucleotide sequences of several Japanese isolates relating both to the structural region and the nonstructural region of the virus (Okamoto et al., (12), Enomoto et al., (4), Kato et al., (6); Takeuchi et al., (15 and 16)). The virus exhibits some similarities with the group comprising Flavi- and Pestiviruses; however, it appears to form a distinct class, different from viruses known up until now (Miller and Purcell, (10)).

In spite of the breakthrough which the cloning of HCV represented, several problems persist:

a substantial genetic variability exists in certain regions of the virus which has made it possible to describe the existence of two groups of viruses, diagnosis of the viral infection remains difficult in spite of the possibility of detecting anti-HCV antibodies in the serum of patients. This is due to the existence of false positive results and to a delayed seroconversion following acute infection. Finally there are clearly cases where only the detection of the virus RNA makes it possible to detect the HCV infection while the serology remains negative.

These problems have important implications both with respect to diagnosis and protection against the virus.

The authors of the present invention have carried out the cloning and obtained the partial nucleotide sequence of a French isolate of HCV (called hereinafter HCV E1) from a blood donor who transmitted an active chronic hepatitis to a recipient. Comparison of the nucleotide sequences and the peptide sequences obtained with the respective sequences of the American and Japanese isolates showed that there was a high conservation of nucleic acids in the noncoding region of HCV E1, a high genetic variability in the structural regions called E1 and E2/NS1, a smaller genetic variability in the nonstructural region.

The present invention is based on new nucleotide and polypeptide sequences of the hepatitis C virus which have not been described in the abovementioned state of the art.

The subject of the present invention is thus a DNA sequence of HCV E1 comprising a DNA sequence chosen from the nucleotide sequences of at least 10 nucleotides between the following nucleotides (n); $n_{118}$ to $n_{138}$; $n_{177}$ to $n_{202}$; $n_{233}$ to $n_{247}$; $n_{254}$ to $n_{272}$ and $n_{272}$ to $n_{288}$ represented in the sequence SEQ ID NO:2, and, $n_{158}$ to $n_{170}$; $n_{170}$ to $n_{217}$; $n_{267}$ to $n_{283}$ and $n_{310}$ to $n_{334}$ represented in the sequence SEQ ID NO:4; as well as analogous nucleotide sequences resulting from degeneracy of the genetic code.

The subject of the invention is in particular the following nucleotide sequences: SEQ ID NO:2, SEQ ID NO:4 and SEQ ID NO:6.

The oligonucleotide sequences may be advantageously synthesised by the Applied Bio System technique.

The subject of the invention is also a peptide sequence of HCV E1 comprising a peptide sequence chosen from the sequences of at least 7 amino acids between the following amino acids (aa): $aa_{58}$ to $aa_{66}$; $aa_{76}$ to $aa_{101}$ represented in the peptide sequence SEQ ID NO:3; $aa_{49}$ to $aa_{78}$; $aa_{98}$ to $aa_{111}$; $aa_{123}$ to $aa_{133}$; $aa_{140}$ to $aa_{149}$ represented in the peptide sequence SEQ ID NO:5; as well as homologous peptide sequences which do not induce modification of biological and immunological properties.

Preferably, the peptide sequence is chosen from the following amino acid sequences: $aa_{58}$ to $aa_{66}$; $aa_{76}$ to $aa_{101}$ represented in the peptide sequence SEQ ID NO:3, $aa_{49}$ to $aa_{78}$; $aa_{98}$ to $aa_{111}$; $aa_{123}$ to $aa_{133}$ and $aa_{140}$ to $aa_{149}$ represented in the peptide sequence SEQ ID NO:5.

Moreover, the peptide sequence is advantageously chosen from the peptide sequences SEQ ID NO:3, SEQ ID NO:5 and SEQ ID NO:7.

The subject of the invention is also a nucleotide sequence encoding a peptide sequence as defined above.

Moreover, the subject of the invention is a polynucleotide probe comprising a DNA sequence as defined above.

The subject of the invention is also an immunogenic peptide comprising a peptide sequence as defined above.

The peptide sequences according to the invention can be obtained by conventional methods of synthesis or by the application of genetic engineering techniques comprising the insertion of a DNA sequence, encoding a peptide sequence according to the invention, into an expression vector such as a plasmid and the transformation of cells using this expression vector and the culture of these cells.

The subject of the invention is also plasmids or expression vectors comprising a DNA sequence encoding a peptide sequence as defined above as well as hosts transformed using this vector.

The preferred plasmids are those deposited with CNCM on 5 Jun. 1991 under the numbers I-1105, I-1106 and I-1107.

The subject of the invention is also monoclonal antibodies directed against a peptide sequence according to the invention or an immunogenic sequence of such a polypeptide.

The monoclonal antibodies according to the invention can be prepared according to a conventional technique. For this purpose, the polypeptides may be coupled, if necessary, to an immunogenic agent such as tetanus anatoxin using a coupling agent such as glutar-aldehyde, a carbodiimide or a bisdiazotised benzidine.

The present invention also encompasses the fragments and the derivatives of monoclonal antibodies according to the invention. These fragments are especially $F(ab')_2$ fragments which can be obtained by enzymatic cleavage of the antibody molecules with pepsin, the Fab' fragments which can be obtained by reducing the disulphide bridges of the $F(ab')_2$ fragments, and the Fab fragments which can be obtained by enzymatic cleavage of the antibody molecules with papain in the presence of a reducing agent. These fragments, as well as the Fc fragments, can also be obtained by genetic engineering.

The derivatives of monoclonal antibodies are for example antibodies or fragments of these antibodies to which markers, such as a radioisotopes, are attached. The derivatives of monoclonal antibodies are also antibodies or fragments of these antibodies to which therapeutically active molecules are attached.

The subject of the invention is also an analytical kit for the detection of nucleotide sequences specific to the HVC E1 strain, comprising one or more probes as defined above.

The subject of the present invention is also an in vitro diagnostic process involving the detection of antigens specific to HCV E1, in a biological sample possibly containing the said antigens, in which, the biological sample is exposed to an antibody or an antibody fragment, as defined above; as well as a diagnostic kit for carrying out the process.

The subject of the invention is also an in vitro diagnostic process involving the detection of antibodies specific to HCV E1 in a biological sample possibly containing the said antibodies, in which a biological sample is exposed to an antigen containing an epitope corresponding to a peptide sequence, as well as a diagnostic kit for the detection of specific antibodies, comprising an antigen containing an epitope corresponding to a peptide sequence as defined above.

These procedures may be based on a radioimmunological method of the RIA, RIPA or IRMA type or an immunoenzymatic method of the WESTERN-BLOT type carried out on strips or of the ELISA type.

The subject of the invention is also a therapeutic composition comprising monoclonal antibodies or fragments of monoclonal antibodies or derivatives of monoclonal antibodies as defined above.

Advantageously, the monoclonal antibody derivatives are monoclonal antibodies or fragments of these antibodies attached to a therapeutically active molecule.

The subject of the invention is also an immunogenic composition containing an immunogenic sequence as defined above, optionally attached to a carrier protein, the said immunogenic sequence being capable of inducing protective antibodies or cytotoxic T lymphocytes. Anatoxins such as tetanus anatoxin may be used as carrier protein. Alternatively, immunogens produced according to the MAP (Multiple Antigenic Peptide) technique may also be used.

In addition to the immunogenic peptide sequence, the immunogenic composition may contain an adjuvant possessing immunostimulant properties.

The following are among the adjuvants which may be used: inorganic salts such as aluminium hydroxide, hydrophobic compounds or surface-active agents such as incomplete Freund's adjuvant, squalene or liposomes, synthetic polynucleotides, microorganisms or microbial components such as murabutide, synthetic artificial molecules such as imuthiol or levamisole, or alternatively cytokines such as interferons $\alpha$, $\beta$, $\gamma$ or interleukins.

The subject of the invention is also a process for assaying a peptide sequence as defined above, comprising the use of monoclonal antibodies directed against this peptide sequence.

The subject of the invention is also a process for preparing a peptide sequence as defined above, comprising the insertion of a DNA sequence, encoding the peptide sequence, into an expression vector, the transformation of cells using this expression vector and the culture of the cells.

The production of the DNA of the sequences of the HCV E1 strain will be described below in greater detail with reference to the accompanying figures in which:

FIG. 2 represents the comparison of the nucleotide sequence of HCV E1 (1) [SEQ ID NO:1], in the non-coding region, with the sequences of an American isolate (2) [SEQ ID NO:24] and two Japanese isolates: HCJ1 (3) [SEQ ID NO:25] and HCJ4 (4) [SEQ ID NO:26] respectively described in WO-A-90/14436 and by Okamoto et al. (12);

FIG. 3 represents the comparison of the nucleotide sequence of HCV E1 (1) [SEQ ID NO:3], in the region E1, with the sequences of an American isolate (HCVpt) (2) [SEQ ID NO:27] described in WO 90/14436 and three Japanese isolates: HCVJ-1 (3) [SEQ ID NO:28], HCJ1 (4) [SEQ ID NO:29] and HCJ4 (5) [SEQ ID NO:30] described in Takeuchi et al. (15); Okamoto et al. (12);

FIG. 4 represents the comparison of the aminoacid sequence, in the region E1, of HCV E1 (1) [SEQ ID NO:3] with the American isolate HCVpt (2) [SEQ ID NO:31] and the Japanese isolates: HCVJ1 (3) [SEQ ID NO:32], HCJ1 (4) [SEQ ID NO:33] and HCJ4 (5) [SEQ ID NO:34]; the variable regions are boxed;

FIG. 5 represents the comparison of the nucleotide sequence, in the region E2/NS1, of HCV E1 (1) [SEQ ID NO:4] with the American isolate HCVpt (2) [SEQ ID NO:35] described in WO-A-90/14436 and the Japanese isolates HCJ1 (3) [SEQ ID NO:36], HCJ4 (4) [SEQ ID NO:37] and HCVJ1 (5) [SEQ ID NO:38] described by Okamoto et al. (12); Takeuchi et al. (15);

FIG. 6 represents a comparison of the aminoacid sequence, in the region E2/NS1, of HCV E1 (1) [SEQ ID NO:5] with the American isolate HCVpt (2) [SEQ ID NO:39] and the Japanese isolates HCJ1 (3) [SEQ ID NO:40], HCJ4 (4) [SEQ ID NO:41] and HCVJ1 (5) [SEQ ID NO:42]; the variable regions are boxed;

FIG. 8 represents the comparison of the nucleotide sequence, in the region NS3/NS4, of HCV E1 (1) [SEQ ID NO:6] with the American isolate HCVpt (2) [SEQ ID NO:43] described in WO-A-90/14436 and the Japanese isolate HCVJ1 (3) [SEQ ID NO:44] described by Kubo et al. (7);

FIG. 9 represents the comparison of the aminoacid sequence, in the region NS3/NS4, of HCV E1 (1) [SEQ ID NO:2] with the American isolate HCVpt (2) [SEQ ID NO:45] and the Japanese isolate HCVJ1 (3) [SEQ ID NO:46].

I—PREPARATION OF THE NUCLEOTIDE SEQUENCES

Figure 1:
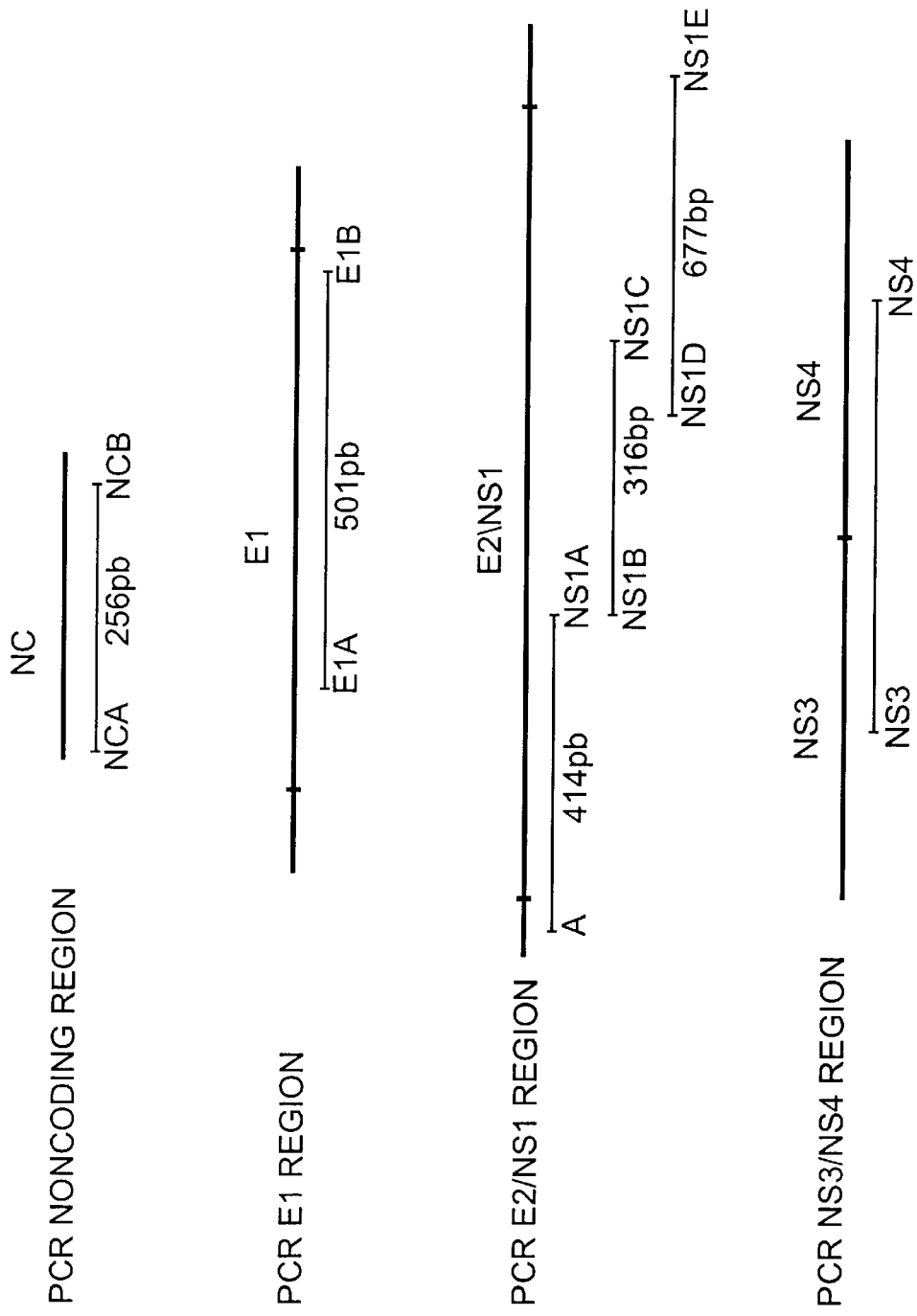
FIG. 1 represents the location of the amplified and sequenced HCV E1 regions.

1) Preparation of the HCV E1 RNA

The HCV E1 RNA was prepared as previously described in EP-A-0,318,216 from the serum of a French blood donor suffering from a chronic hepatitis, anti-HCV positive (anti-C100) (Kubo et al. (7)).

100 $\mu$l of serum were diluted in a final volume of 1 ml, in the following extraction buffer: 50 mM tris-HCl, pH.8, 1 mM EDTA, 100 mM NaCl, 1 mg/ml of proteinase K, and 0.5% SDS. After digestion with proteinase K for 1 h at 37° C., the proteins were extracted with one volume of TE-saturated phenol (10 mM Tris-HCl, pH.8, 1 mM EDTA). The aqueous phase was then extracted twice with one volume of phenol/chloroform (1:1) and once with one volume of chloroform. The aqueous phase was then adjusted to a final concentration of 0.2M sodium acetate and the nucleic acids were precipitated by the addition of two volumes of ethanol. After centrifugation, the nucleic acids were suspended in 30 $\mu$l of DEPC-treated sterile distilled water.

2) Reverse transcription and amplification

A complementary DNA (cDNA) was synthesised using as primer either oligonucleotides specific to HCV, represented in Table I below, or a mixture of hexanucleotides not specific to HCV, and murine reverse transcriptase. A PCR (Polymerase Chain Reaction) was carried out over 40 cycles at the following temperatures: 94° C. (1 min), 55° C. (1 min), 72° C. (1 min), on the cDNA thus obtained, using pairs of primers specific to HCV (Table I below). Various HCV primers were made from the sequence of HCV prototype (HCVpt), isolated from a chronically infected chimpanzee (Bradley et al. (2); Alter et al. (1), EP-A-0,318,216). The nucleotide sequence of the 5' region of the E2/NS1 gene was obtained using a strategy derived from the sequence-independent single primer amplification technique (SISPA) described by Reyes et al. (13). It consists in ligating double-stranded adaptors to the ends of the DNA synthesised using an HCV-specific primer localised in 5' of the HCVpt sequence (primer NS1A in Table I). A semi-specific amplification is then carried out using an HCV-specific primer as well as a primer corresponding to the adaptor. This approach makes it possible to obtain amplification products spanning the 5' region of the primer used for the synthesis of the cDNA.

1) Nucleotide sequence of HCV E1 in the noncoding 5' region

Figure 2:
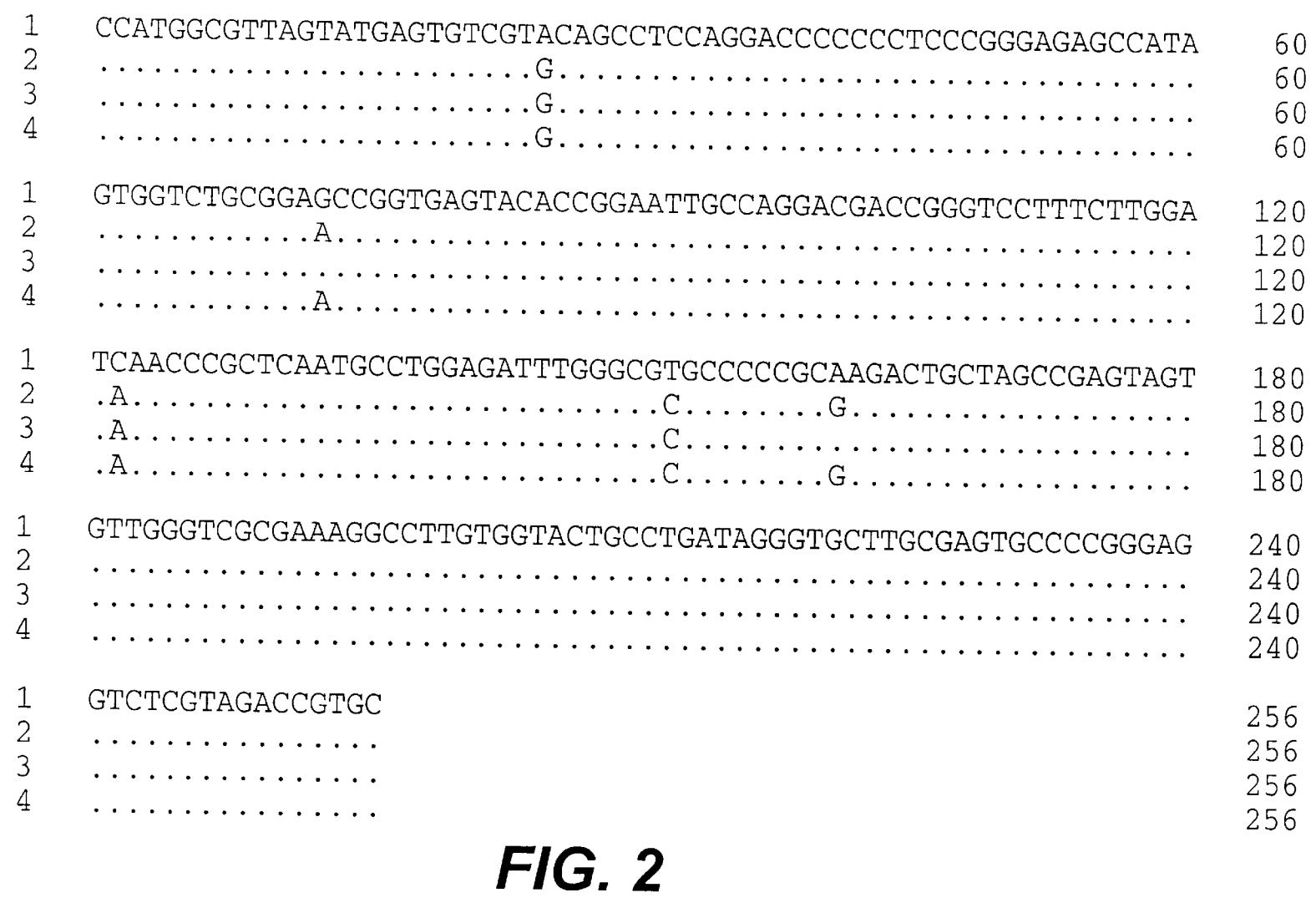

The amplified and sequenced noncoding 5' region of HCV E1 is called SEQ ID No.1. It corresponds to a 256-base pair (bp) fragment located in position −259 to −4 in HCVpt as described in WO-A-90/14436. Comparison of the HCV E1 sequence with those previously published shows a very high nucleic acid conservation (FIG. 2).

2) Nucleotide and peptide sequences of HCV E1 in the structural region

The nucleotide sequences probably correspond to two regions encoding the virus envelope proteins (currently designated as the E1 and E2/NS1 regions).

For the E1 region, the sequence obtained for HCV E1 corresponds to the 3' moiety of the gene. It has been called SEQ ID No.2. This 501-bp sequence is located in position 470 and 973 in the HCVpt sequence as described in WO-A-90/14436. Comparison of this sequence with those previously described shows a high genetic variability (FIG. 3). Indeed, depending on the isolates studied, a difference of 10 to 27% in nucleic acid composition and 7 to 20% in amino acid composition may be observed as shown in Table II below. Furthermore, comparison of the peptide sequence

TABLE I

Sequence of the primers and probes.

a) Primers[a]:

| | | |
|---|---|---|
| NS3 | (+) 5' ACAATACGTGTGTCACC (3013–3029) | [SEQ ID NO: 8] |
| NS4 | (−) 5' AAGTTCCACATATGCTTCGC (3955–3935) | [SEQ ID NO: 9] |
| NS1A | (−) 5' TCCCTTCGCATAACTCATAG (83–64) | [SEQ ID NO: 10] |
| NS1B | (+) 5' CTATCAGTTATGCCAACCGA (64–83) | [SEQ ID NO: 11] |
| NS1C | (−) 5' CTTGCCCGCCCCTCCGATGT (380–361) | [SEQ ID NO: 12] |
| NS1D | (+) 5' CCCAGCCCCGTGGTGGTGGG (183–202) | [SEQ ID NO: 13] |
| NS1E | (−) 5' CCACAAGCAGGAGCAGACGC (860–841) | [SEQ ID NO: 14] |
| NCA | (+) 5' CCATGGCGTTAGTATGAGT (−259− −239) | [SEQ ID NO: 15] |
| NCB | (−) 5' GCAGGTCTACGAGACCTC (−4− −23) | [SEQ ID NO: 16] |
| E1A | (+) 5' TTCTGGAACACGCCGTGAAC (470–489) | [SEQ ID NO: 17] |
| E1B | (−) 5' TCATCATATCCCATGCCATG (973–954) | [SEQ ID NO: 18] | b) probes[a]:

| | | |
|---|---|---|
| NS3/NS4 | (+) 5' CCTTCACCATTGAGACAATCACGCTCCCCCAGGATGCTGT (3058–3097) | [SEQ ID NO: 19] |
| NS1 | (+) 5' CTGTCCTGAGAGGCTAGCCAGCTGCCGACCCCTTACCGAT (5–44) | [SEQ ID NO: 20] |
| NS1B/C | (+) 5' AGCTCGCGCGCGCCCACCTACAGCTGGGGTGAAAATGATA (210–248) | [SEQ ID NO: 21] |
| NC | (+) 5' GTCCACCCTCCAGGACCCCC (235− −216) | [SEQ ID NO: 22] |
| E1 | (−) 5' CTCGTACACAATACTCGAGT (646–627) | [SEQ ID NO: 23] |

[a]The nucleotide sequences and their locations correspond to the HCV prototype (HCVpt) (EP-A-0, 318, 216 and WO-A-90/14436).

3) Cloning and sequencing

The amplification products were cloned into M13 mp19 or into the bacteriophage lambda gt 10 as described by Thiers et al. (17). The probes used for screening the DNA sequences are represented in Table I above. The nucleotide sequence of the inserts was determined by the dideoxynucleotide-based method described by Sanger et al., (14).

II—STUDY OF THE NUCLEOTIDE SEQUENCES OF THE FRENCH ISOLATE (HCV E1)

The location of the various amplification products which made it possible to obtain the nucleotide sequence of the HCV E1 isolate in nonstructural and structural regions as well as in the noncoding region of the virus, is schematically represented in FIG. 1.

reveals the existence of two hypervariable regions which are boxed in FIG. 4.

Figure 6A:
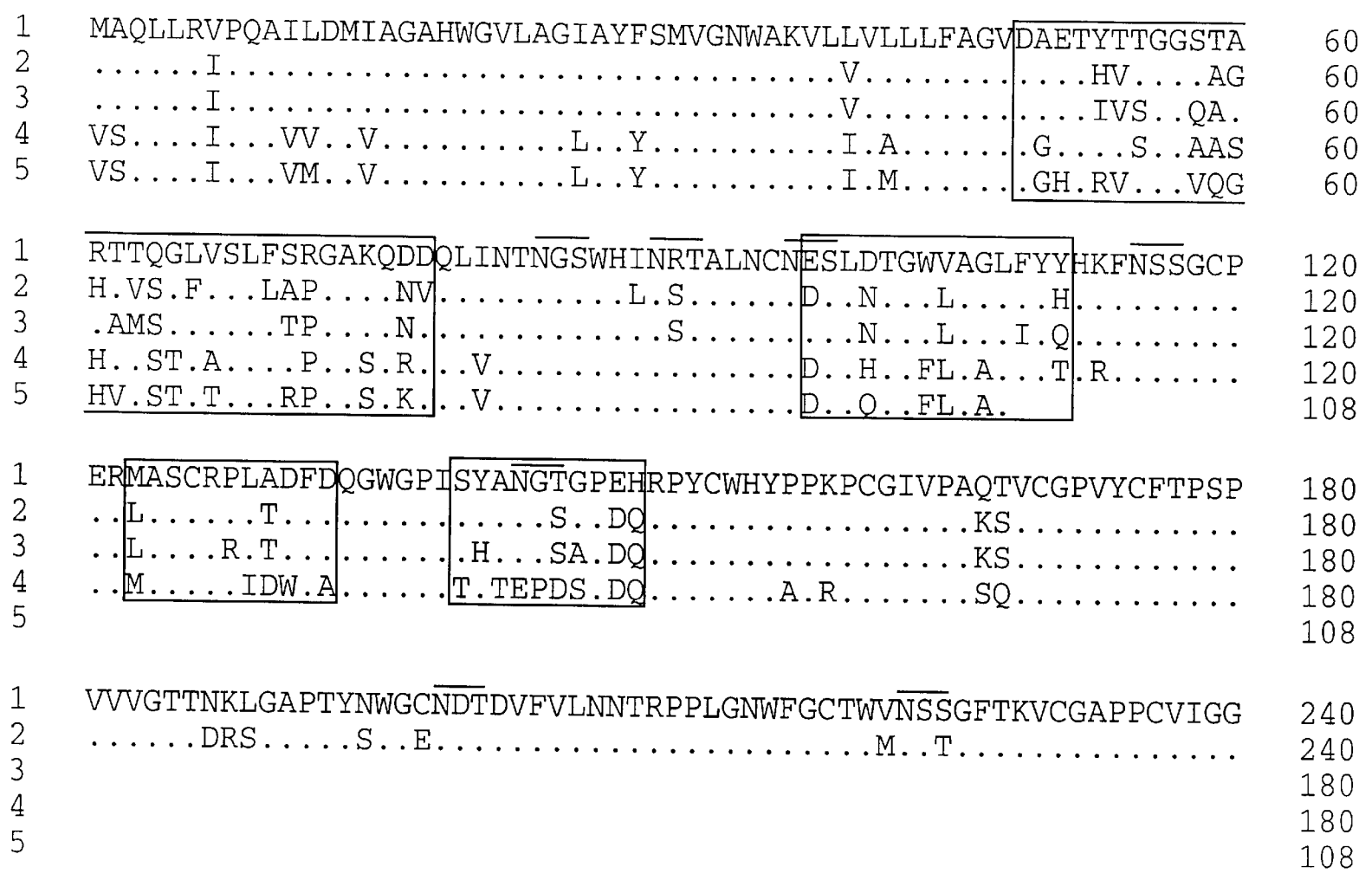
Figure 7:
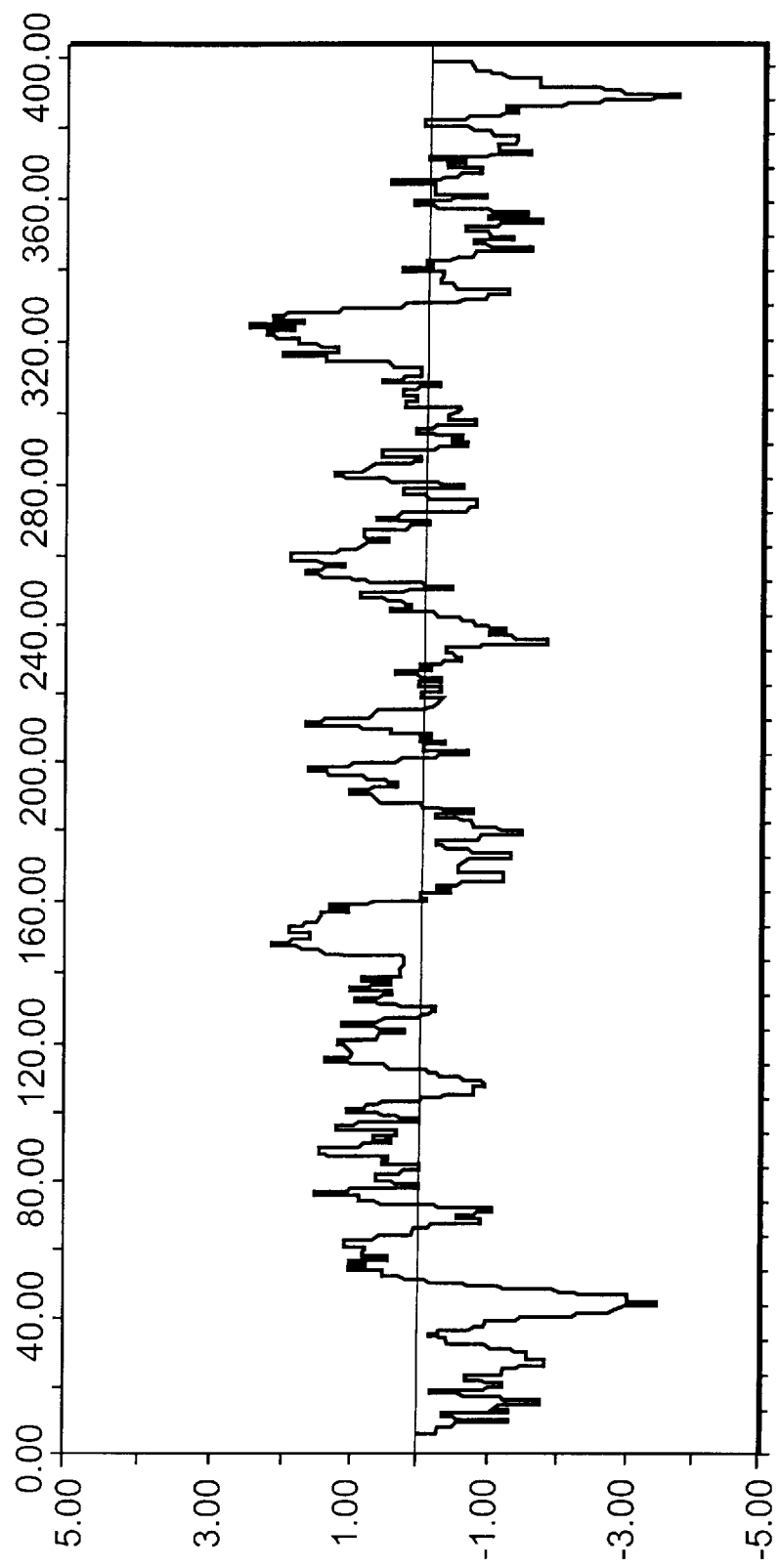
FIG. 7 represents the hydrophilicity profile of HCV E1 in the region E2/NS1; the hydrophobic regions are located under the middle line.

For the E2/NS1 region, the HVC E1 sequence data were obtained from three overlapping amplification products (FIG. 1). The consensus sequence thus obtained (1210 bp) contains the entire E2/NS1 gene and was called SEQ ID No.3. The sequence of the E2/NS1 region of HCV E1 is situated in position 999 and 2209 compared with the HCVpt sequence described in WO-A-90/14436. Comparison of the HCV E1 sequences with the isolates previously described shows a difference of 13 to 33% in the case of nucleic acids and 11 to 30% in the case of amino acids (FIG. 5 and 6, Table II). The highest variability is observed in 5' of the E2/NS1 gene (FIG. 5). Comparison of amino acids shows the existence of four hypervariable regions which are boxed in FIG. 6. The hydrophilicity profile of the E2/NS1 region (Kyte and Dolittle, (9)) is given in FIG. 7. A hydrophilic region flanked by two hydrophobic regions are observed. Both hydrophobic regions probably correspond to the signal sequence as well as to the transmembrane segment. Finally, the central region has ten potential glycolisation [sic] sites (N-X-T/S), which are conserved in the various isolates (FIG. 6).

3) Nucelotide and peptide sequence of HCV E1 in the nonstructural region

The sequence data for HCV E1 in the nonstructural region correspond to the 3' and 5' terminal parts of the NS3 and NS4 genes respectively (FIG. 1). The sequence obtained for HCV E1 (943 bp) is located in position 4361 to 5303 in the HCVpt sequence and was called SEQ ID No.4. The sequence homology is 95% with the HCVpt isolate and 78.6% with a Japanese isolate (FIG. 8, Table II above). In the case of the comparison of amino acids, a homology of 98% and 93% was observed with the HCVpt and Japanese isolates respectively (FIG. 8, Table II above).

Thus, comparison of the nucleotide sequence of the HCV E1 isolate with that of the American and Japanese isolates shows that the French isolate is different from the isolates described above. It reveals the existence of highly variable regions in the envelope proteins. The variability of the nonstructural region studied is lower. Finally, the noncoding 5' region shows a high conservation.

These results have implications both for diagnosis and prevention of HVC.

As far as diagnosis is concerned, definition of the hypervariable regions and of the conserved regions can lead to:

the definition of synthetic peptides which allow the expression of epitopes specific to the various HCV groups.

For the envelope protein E1, peptides for the determination of type-specific epitopes are advantageously defined in a region between amino acids 75 to 100 (FIG. 4). Likewise, for the protein E2/NS1, peptides allow [sic] characterisation of specific epitopes are synthesised in regions preferably between amino acids 50 and 149, (FIG. 6).

The expression of all or part of the cloned sequences, in particular clones corresponding to the envelope regions of the virus, make it possible to obtain new antigens for the development of diagnostic reagents and for the production of immunogenic compositions. Finally, the preparation of a substantial part of the nucleotide sequence of this isolate allows the production of the entire length of complementary DNA which can be used for a better understanding of the mechanisms of the viral infection and also for diagnostic and preventive purposes.

TABLE II

Difference in nucleic acids (n.a.) and amino acids (a.a.) between the French isolate (HCV E1) and the American (HCVpt) and japanese (HCVJ1, HCJ1, HCJ4) isolates.

|  |  | HCVpt | HCVJ1 | HCJ1 | HCJ4 |
|---|---|---|---|---|---|
| HCVE1 E1 | n.a. | 10.6 | 27.3 | 10.4 | 26.5 |
|  | a.a. | 7.2 | 19.9 | 8.4 | 20.5 |
| HCVE1 E2/NS1 | n.a. | 12.8% | 33.2% | 14.5% | 29.8% |
|  | a.a. | 12.2% | 29.7% | 15.6% | 26.1% |
| HCVE1 NS3/NS4 | n.a. | 5.2% | 21.4% | — | — |
|  | a.a. | 2.2% | 6.9% | — | — |

REFERENCES

1. Alter, H. J., Purcell, R. H., Shib, J. W., Melpolder, J. C., Houghton, M., Choo, Q. -L. & Kuo, G. (1989). Detection of antibody to hepatitis C virus in prospectively followed transfusion recipients with acute and chronic Non-A, Non-B hepatitis. New England Journal of Medicine 321, 1494–1500.
2. Bradley, D. W., Cook, E. H., Maynard, J. E., McCaustland, K. A., Ebert, J. W., Dolana, G. H., Petzel, R. A., Kantor, R. J., Heilbrunn, A., Fields, H. A. & Murphy, B. L. (1979). Experimental infection of chimpanzees with antihemophilic (factor VIII) materials: recovery of virus-like particles associated with Non-A, Non-B hepatitis. Journal of Medical Virology 3, 253–269.
3. Choo, Q. -L., Kuo, G., Weiner, A. J., Overby, L. R., Bradley, D. W. & Houghton, M. (1989). Isolation of a cDNA clone derived from a blood-borne Non-A, Non-B viral hepatitis genome. Science 244, 359–362.
4. Enomoto, N., Takada, A., Nakao, T. & Date, T. (1990). There are two major types of hepatitis C virus in Japan. Biochemical and Biophysical Research Communications 170, 1021–1025.
5. Hopf, U., Möller, B., Küther, D., Stemerowicz, R., Lobeck, H., Lüdtke-Handjery, A., Walter, E., Blum, H. E., Roggendorf, M. & Deinhardt, F. (1990). Long-term follow-up of post transfusion and sporadic chronic hepatitis Non-A, Non-B and frequency of circulating antibodies to hepatitis C virus (HCV). Journal of Hepatology 10, 69–76.
6. Kato, N., Hijakata, M., Ootsuyama, Y., Nakagawa, M., Ohkoshi, S., Sugimura, T. & Shimotohno, K. (1990). Molecular cloning of the human hepatitis C virus genome from Japanese patients with Non-A, Non-B hepatitis. Proceedings of the National Academy of Sciences, U.S.A. 87, 9524–9528.
7. Kubo, Y., Takeuchi, K., Boonmar, S., Katayama, T., Choo, Q. -L., Kuo, G., Weiner, A. J., Bradley D. W., Houghton, M., Saito, I. & Miyamura, T. (1989). A cDNA fragment of hepatitis C virus isolated from an implicated donor of post-transfusion Non-A, Non-B hepatitis in Japan. Nucleic Acids Research 17, 10367–10372.
8. Kuo, G., Choo, Q. -L., Alter, H. J., Gitnick, G. L., Redeker, A. G., Purcell, R. H., Miyamura, T., Dienstag, J. L., Alter, M. J., Stevens, C. E., Tegtmeier, G. E., Bonino, F., Colombo, M., Lee, W. S., Kuo, C., Berger, K., Shuster, J. R., Overby, L. R., Bradley, D. W. & Houghton, M. (1989). An assay for circulating antibodies to a major etiologic virus of human Non-A, Non-B hepatitis. Science 244, 362–364.
9. Kyte, W. & Doolittle, R. F. (1982). A simple method for displaying the hydropathic of a protein. Journal of Molecular Biology 157, 105–132.
10. Miller, R. H. & Purcell, R. H. (1990). Hepatitis C virus shares amino acid sequence similarity with pestiviruses and flaviviruses as well as members of two plant virus super groups. Proceedings of the National Academy of Sciences, U.S.A. 87, 2057–2061.
11. Miyamura, T., Saito, T., Katayama, T., Kikuchi, S., Tateda, A., Houghton, M., Choo, Q. -L. & Kuo, G. (1990). Detection of antibody against antigen expressed by molecularly cloned hepatitis C virus cDNA: application to diagnosis and blood screening for posttransfusion hepatitis. Proceedings of the National Academy of Sciences, U.S.A. 87, 983–987.
12. Okamoto, H., Okada, S., Sugiyama, Y., Yotsumoto, S., Tanaka, T., Yoshizawa, H., Tsuda, F., Miyakawa, Y. & Mayumi, M. (1990). The 5' terminal sequence of the hepatitis C virus genome. Japanese Journal of Experimental Medicine 60, 167–177.
13. Reyes, G. R., Purdy, M. A., Kim, J. P., Luk, K. -C., Young, L. M., Fry, K. E. & Bradley, D. W. (1990). Isolation of a cDNA from the virus responsible for enterically transmitted Non-A, Non-B hepatitis. Science 247, 1335–1339.
14. Sanger, F. S., Nicklen, S. & Coulsen, A. R. (1977). DNA sequencing with chain terminating inhibition. Proceedings of the National Academy of Sciences, U.S.A. 74, 5463–5467.
15. Takeuchi, K., Boonmar, S., Kubo, Y., Katayama, T., Harada, H., Ohbayashi, A., Choo, Q., -L., Houghton, M., Saito, I. & Miyamura, T. (1990a). Hepatitis C viral cDNA clones isolated from a healthy carrier donor implicated in post-transfusion Non-A, Non-B hepatitis. Gene 91 (2), 287–291.
16. Takeuchi, K., Kubo, Y., Boonmar, S., Watanabe, Y., Katayama, T., Choo, Q. -L., Kuo, G., Houghton, M., Saito, I. & Miyamura, T. (1990b). Nucleotide sequence of core and envelope genes of the hepatitis C virus genome derived directly from human healthy carriers. Nucleic Acids Research 18, 4626.
17. Thiers, V., Nakajima, E. N., Kremsdorf, D., Mack, D., Schellekens, H., Driss, F., Goude, A., Wands, J., Sninsky, J., Tiollais, P. & Brechot, C. (1988). Transmission of hepatitis B from hepatitis B seronegative subjects. Lancet ii, 1273–1276.

| Symbols for the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

We claim:

1. An immunogenic composition comprising a purified HCV E1 peptide, wherein said peptide has 7 amino acids of an amino acid sequence selected from the group consisting of:
   (a) $aa_{58}$ to $aa_{66}$ of SEQ ID NO:3;
   (b) $aa_{49}$ $aa_{78}$ of SEQ ID NO:5; and
   (c) $aa_{123}$ to $aa_{133}$ of SEQ ID NO:5.

2. The immunogenic composition of claim 1, wherein said immunogenic composition comprises a carrier protein.

3. The immunogenic composition of claim 2, wherein said carrier protein is attached to said peptide.

4. The immunogenic composition of claim 3, wherein said immunogenic composition induces protective antibodies.

5. A diagnostic kit for detecting HCV E1-specific antibodies, wherein said kit comprises:
   (i) an antigen, wherein said antigen has 7 amino acids of an amino acid sequence selected from the group consisting of:
      (a) $aa_{58}$ to $aa_{66}$ of SEQ ID NO:3;
      (b) $aa_{49}$ $aa_{78}$ of SEQ ID NO:5; and
      (c) $aa_{123}$ to $aa_{133}$ of SEQ ID NO:5; and
   (ii) a reagent for detecting said antigen-antibody complex.

6. The kit of claim 5, wherein said antigen is labeled.

7. An immunogenic composition comprising a purified HCV E1 peptide, wherein said peptide has an amino acid sequence selected from the group consisting of:
   (a) SEQ ID NO:3;
   (b) SEQ ID NO:5; and
   (c) SEQ ID NO:7.

8. The immunogenic composition of claim 7, wherein said immunogenic composition comprises a carrier protein.

9. The immunogenic composition of claim 8, wherein said carrier protein is attached to said peptide.

10. The immunogenic composition of claim 9, wherein said immunogenic composition induces protective antibodies.

11. A diagnostic kit for detecting HCV E1-specific antibodies, wherein said kit comprises:
   (i) an antigen, wherein said antigen has an amino acid sequence selected from the group consisting of:
      (a) SEQ ID NO:3;
      (b) SEQ ID NO:5; and
      (c) SEQ ID NO:7;
   wherein said antigen binds with an antibody, forming an antigen-antibody complex; and
   (ii) a reagent for detecting said antigen-antibody complex.

12. The kit of claim 11, wherein said antigen is labeled.

13. An immunogenic composition comprising a purified HCV E1 peptide, wherein said peptide has an amino acid sequence selected from the following:
   (a) $aa_{58}$ to $aa_{66}$ of SEQ ID NO:3;
   (b) $aa_{49}$ $aa_{78}$ of SEQ ID NO:5; and
   (c) $aa_{123}$ to $aa_{133}$ of SEQ ID NO:5.

14. The immunogenic composition of claim 13, wherein said immunogenic composition comprises a carrier protein.

15. The immunogenic composition of claim 14, wherein said carrier protein is attached to said peptide.

16. The immunogenic composition of claim 15, wherein said immunogenic composition induces protective antibodies.

17. A diagnostic kit for detecting HCV E1-specific antibodies, wherein said kit comprises:
   (i) an antigen, wherein said antigen has an amino acid sequence selected from the following:
      (a) $aa_{58}$ to $aa_{66}$ of SEQ ID NO:3;
      (b) $aa_{49}$ $aa_{78}$ of SEQ ID NO:5; and
      (c) $aa_{123}$ to $aa_{133}$ of SEQ ID NO:5;
   wherein said antigen binds with an antibody, forming an antigen-antibody complex; and
   (ii) a reagent for detecting said antigen-antibody complex.

18. The kit of claim 17, wherein said antigen is labeled.

19. A purified HCV E1 peptide, wherein said peptide has 7 amino acids of an amino acid sequence selected from the group consisting of:
   (a) $aa_{58}$ to $aa_{66}$ of SEQ ID NO:3;
   (b) $aa_{49}$ $aa_{78}$ of SEQ ID NO:5; and
   (c) $aa_{123}$ to $aa_{133}$ of SEQ ID NO:5.

20. A purified HCV E1 peptide wherein said peptide has an amino acid sequence selected from the group consisting of:
   (a) $aa_{58}$ to $aa_{66}$ of SEQ ID NO:3;
   (b) $aa_{49}$ $aa_{78}$ of SEQ ID NO:5; and
   (c) $aa_{123}$ to $aa_{133}$ of SEQ ID NO:5.

21. A purified HCV E1 peptide, wherein said peptide has an amino acid sequence selected from the group consisting of:
   (a) SEQ ID NO:3;
   (b) SEQ ID NO:5; and
   (c) SEQ ID NO:7.

* * * * *

UNITED STATES PATENT AND TRADEMARK OFFICE
CERTIFICATE OF CORRECTION

PATENT NO. : 5,866,139

DATED : February 2, 1999

INVENTOR(S) : Brechot et al.

It is certified that error appears in the above-identified patent and that said Letters Patent is hereby corrected as shown below:

Cover page (left column), item [62], after "Division of Ser. No. 965,285, Mar. 18, 1993", insert:

--, which was a National Stage of International Application No. PCT/FR92/00501, filed June 4, 1992--.

Column 1, line 7, after "filed March 18, 1993", please insert:

--, which was a National Stage of International Application No. PCT/FR92/00501, filed June 4, 1992--.

Signed and Sealed this

Twenty-eighth Day of November, 2000

Attest:

*Attesting Officer*

Q. TODD DICKINSON

*Director of Patents and Trademarks*

UNITED STATES PATENT AND TRADEMARK OFFICE
CERTIFICATE OF CORRECTION

PATENT NO. : 5,866,139
DATED : February 2, 1999
INVENTOR(S) : Brechot et al.

It is certified that error appears in the above-identified patent and that said Letters Patent is hereby corrected as shown below:

Title page the following should be inserted:

--[30]  Foreign Application Priority Data

Jun. 6, 1991  [FR]  France..................................91 06882--

Signed and Sealed this

Twenty-eighth Day of November, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 256 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:1:

```
CCATGGCGTT  AGTATGAGTG  TCGTACAGCC  TCCAGGACCC  CCCCTCCGG   GAGAGCCATA    60
GTGGTCTGCG  GAGCCGGTGA  GTACACCGGA  ATTGCCAGGA  CGACCGGGTC  CTTTCTTGGA   120
TCAACCCGCT  CAATGCCTGG  AGATTTGGGC  GTGCCCCGC   AAGACTGCTA  GCCGAGTAGT   180
GTTGGGTCGC  GAAAGGCCTT  GTGGTACTGC  CTGATAGGGT  GCTTGCGAGT  GCCCCGGGAG   240
GTCTCGTAGA  CCGTGC                                                      256
```

( 2 ) INFORMATION FOR SEQ ID NO:2:

( i ) SEQUENCE CHARACTERISTICS:
        ( A ) LENGTH: 501 base pairs
        ( B ) TYPE: nucleic acid
        ( C ) STRANDEDNESS: single (D) TOPOLOGY: linear (i i) MOLECULE TYPE: Other
(A) DESCRIPTION: cDNA to genomic RNA (x i) SEQUENCE DESCRIPTION: SEQ ID NO:2:

| TTCTGGAAGA | CGGCGTGAAC | TATGCAACAG | GGAACCTTCC | TGGTTGCTCT | TTCTCTATCC | 60 |
|---|---|---|---|---|---|---|
| TCCTCCTGGC | CCTGCTCTCT | TGCCTGACTG | TGCCCGCGTC | AGCCTACCAA | GTACGCAATT | 120 |
| CTCGCGGCCT | TTACCATGTC | ACCAATGATT | GCCCTAACTC | GAGTATTGTG | TACGAGACGG | 180 |
| CCGATAGCAT | TCTACACTCT | CCGGGGTGTG | TCCCTTGCGT | TCGCGAGGGT | AACACCTCGA | 240 |
| AATGTTGGGT | GGCGGTGGCC | CCTACAGTCG | CCACCAGAGA | CGGCAGACTC | CCCACAACGC | 300 |
| AGCTTCGACG | TCATATCGAT | CTGCTCGTCG | GGAGCGCCAC | CCTCTGCTCG | GCCCTCTATG | 360 |
| TGGGGACTT  | GTGCGGGTCC | GTCTTCCTCG | TCGGTCAATT | GTTCACCTTC | TCCCCCAGGC | 420 |
| GCCACTGGAC | AACGCAAGAC | TGCAACTGTT | CCATCTACCC | CGGCCACGTA | ACGGGTCACC | 480 |
| GCATGGCATG | GGATATGATG | A | | | | 501 |

(2) INFORMATION FOR SEQ ID NO:3:

(i) SEQUENCE CHARACTERISTICS:
(A) LENGTH: 166 amino acids
(B) TYPE: amino acid
(D) TOPOLOGY: linear (i i) MOLECULE TYPE: peptide (x i) SEQUENCE DESCRIPTION: SEQ ID NO:3:

| Leu | Glu | Asp | Gly | Val | Asn | Tyr | Ala | Thr | Gly | Asn | Leu | Pro | Gly | Cys | Ser |
|---|---|---|---|---|---|---|---|---|---|---|---|---|---|---|---|
| 1 | | | | 5 | | | | | 10 | | | | | 15 | |
| Phe | Ser | Ile | Leu | Leu | Leu | Ala | Leu | Leu | Ser | Cys | Leu | Thr | Val | Pro | Ala |
| | | | 20 | | | | | 25 | | | | 30 | | | |
| Ser | Ala | Tyr | Gln | Val | Arg | Asn | Ser | Arg | Gly | Leu | Tyr | His | Val | Thr | Asn |
| | | 35 | | | | | 40 | | | | | 45 | | | |
| Asp | Cys | Pro | Asn | Ser | Ser | Ile | Val | Tyr | Glu | Thr | Ala | Asp | Ser | Ile | Leu |
| | 50 | | | | | 55 | | | | | 60 | | | | |
| His | Ser | Pro | Gly | Cys | Val | Pro | Cys | Val | Arg | Glu | Gly | Asn | Thr | Ser | Lys |
| 65 | | | | | 70 | | | | | 75 | | | | | 80 |
| Cys | Trp | Val | Ala | Val | Ala | Pro | Thr | Val | Ala | Thr | Arg | Asp | Gly | Arg | Leu |
| | | | | 85 | | | | | 90 | | | | | 95 | |
| Pro | Thr | Thr | Gln | Leu | Arg | Arg | His | Ile | Asp | Leu | Leu | Val | Gly | Ser | Ala |
| | | | 100 | | | | | 105 | | | | | 110 | | |
| Thr | Leu | Cys | Ser | Ala | Leu | Tyr | Val | Gly | Asp | Leu | Cys | Gly | Ser | Val | Phe |
| | | 115 | | | | | 120 | | | | | 125 | | | |
| Leu | Val | Gly | Gln | Leu | Phe | Thr | Phe | Ser | Pro | Arg | Arg | His | Trp | Thr | Thr |
| | | 130 | | | | 135 | | | | | 140 | | | | |
| Gln | Asp | Cys | Asn | Cys | Ser | Ile | Tyr | Pro | Gly | His | Val | Thr | Gly | His | Arg |
| 145 | | | | | 150 | | | | | 155 | | | | | 160 |
| Met | Ala | Trp | Asp | Met | Met |
| | | | | 165 | |

(2) INFORMATION FOR SEQ ID NO:4:

(i) SEQUENCE CHARACTERISTICS:
(A) LENGTH: 1210 base pairs
(B) TYPE: nucleic acid
(C) STRANDEDNESS: single
(D) TOPOLOGY: linear (i i) MOLECULE TYPE: Other (A) DESCRIPTION: cDNA to genomic RNA (xi) SEQUENCE DESCRIPTION: SEQ ID NO:4:

```
AATGGCTCAA CTGCTCAGGG TCCCGCAAGC CATCTTGGAC ATGATCGCTG GTGCCCACTG        60
GGGAGTCCTA GCGGGCATAG CGTATTTCTC CATGGTGGGG AACTGGGCGA AGGTCCTGCT       120
AGTGCTGTTG CTGTTCGCCG GCGTCGATGC GGAAACCTAC ACCACCGGGG GGAGTACTGC       180
CAGGACCACG CAAGGACTCG TCAGCCTTTT CAGTCGAGGC GCCAAGCAGG ACATCCAGCT       240
GATCAACACC AACGGCAGCT GGCACATTAA TCGCACAGCT TTGAACTGTA ATGAGAGCCT       300
CGACACCGGC TGGGTAGCGG GGCTCTTCTA TTACCACAAA TTCAACTCTT CAGGCTGCCC       360
CGAGAGGATG GCCAGCTGCA GACCCCTTGC CGATTTCGAC CAGGGCTGGG GCCCTATCAG       420
TTATGCCAAC GGAACCGGCC CTGAACACCG CCCCTACTGC TGGCACTACC CCCCAAAGCC       480
TTGTGGTATC GTGCCAGCAC AGACCGTATG TGGCCCAGTG TATTGCTTCA CTCCTAGCCC       540
CGTGGTGGTG GGGACGACCA ATAAGTTGGG CGCACCCACT TACAACTGGG GTTGTAATGA       600
TACGGACGTC TTCGTCCTTA ATAACACCAG GCCACCGCTG GGCAATTGGT TCGGCTGCAC       660
CTGGGTGAAC TCATCTGGAT TTACTAAAGT GTGCGGAGCG CCTCCCTGTG TCATCGGAGG       720
AGCGGGCAAT AACACCTTGT ACTGCCCCAC TGACTGTTTC CGCAAGCATC CGGAAGCTAC       780
ATACTCCCGA TGTGGCTCCG GTCCTTGGAT CACGCCCAGG TGCCTGGTTG CTATCCTTA       840
TAGGCTCTGG CATTATCCCT GTACTGTCAA CTACACCCTG TTCAAGGTCA GGATGTACGT       900
GGGAGGGGTC GAGCACAGGC TGCAAGTCGC TTGCAACTGG ACGCGGGGCG AGCGTTGTAA       960
TCTGGACGAC AGGGACAGGT CCGAGCTCAG TCCGCTGCTG CTGTCTACCA CACAGTGGCA      1020
GGTCCTCCCG TGTTCCTTTA CGACCTTGCC AGCCTTGACT ACCGGCCTCA TCCACCTCCA      1080
CCAGAACATC GTGGACGTGC AATATTTGTA CGGGGTGGGG TCAAGCATTG TGTCCTGGGC      1140
CATCAAGTGG GAGTACGTCA TTCTCCTGTT TCTCCTGCTT GCAGACGCGC GCGTCTGCTC      1200
CTGCTTGTGG                                                             1210
```

(2) INFORMATION FOR SEQ ID NO:5:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Ala Gln Leu Leu Arg Val Pro Gln Ala Ile Leu Asp Met Ile Ala
 1               5                  10                  15
Gly Ala His Trp Gly Val Leu Ala Gly Ile Ala Tyr Phe Ser Met Val
            20                  25                  30
Gly Asn Trp Ala Lys Val Leu Val Leu Leu Leu Phe Ala Gly Val
        35                  40                  45
Asp Ala Glu Thr Tyr Thr Thr Gly Gly Ser Thr Ala Arg Thr Thr Gln
    50                  55                  60
Gly Leu Val Ser Leu Phe Ser Arg Gly Ala Lys Gln Asp Ile Gln Leu
65                  70                  75                  80
Ile Asn Thr Asn Gly Ser Trp His Ile Asn Arg Thr Ala Leu Asn Cys
                85                  90                  95
Asn Glu Ser Leu Asp Thr Gly Trp Val Ala Gly Leu Phe Tyr Tyr His
               100                 105                 110
```

| | | | | | | | | | | | | | |
|---|---|---|---|---|---|---|---|---|---|---|---|---|---|
|Lys|Phe|Asn 115|Ser|Ser|Gly|Cys|Pro 120|Glu|Arg|Met|Ala|Ser 125|Cys|Arg|Pro|
|Leu|Ala 130|Asp|Phe|Asp|Gln|Gly 135|Trp|Gly|Pro|Ile|Ser 140|Tyr|Ala|Asn|Gly|
|Thr 145|Gly|Pro|Glu|His|Arg 150|Pro|Tyr|Cys|Trp|His 155|Tyr|Pro|Pro|Lys|Pro 160|
|Cys|Gly|Ile|Val|Pro 165|Ala|Gln|Thr|Val|Cys 170|Gly|Pro|Val|Tyr|Cys 175|Phe|
|Thr|Pro|Ser|Pro 180|Val|Val|Val|Gly|Thr 185|Thr|Asn|Lys|Leu|Gly 190|Ala|Pro|
|Thr|Tyr|Asn 195|Trp|Gly|Cys|Asn|Asp 200|Thr|Asp|Val|Phe|Val 205|Leu|Asn|Asn|
|Thr|Arg 210|Pro|Pro|Leu|Gly|Asn 215|Trp|Phe|Gly|Cys|Thr 220|Trp|Val|Asn|Ser|
|Ser 225|Gly|Phe|Thr|Lys|Val 230|Cys|Gly|Ala|Pro|Pro 235|Cys|Val|Ile|Gly|Gly 240|
|Ala|Gly|Asn|Asn|Thr 245|Leu|Tyr|Cys|Pro|Thr 250|Asp|Cys|Phe|Arg|Lys 255|His|
|Pro|Glu|Ala|Thr 260|Tyr|Ser|Arg|Cys|Gly 265|Ser|Gly|Pro|Trp|Ile 270|Thr|Pro|
|Arg|Cys|Leu 275|Val|Gly|Tyr|Pro|Tyr 280|Arg|Leu|Trp|His|Tyr 285|Pro|Cys|Thr|
|Val|Asn 290|Tyr|Thr|Leu|Phe|Lys 295|Val|Arg|Met|Tyr|Val 300|Gly|Gly|Val|Glu|
|His 305|Arg|Leu|Gln|Val|Ala 310|Cys|Asn|Trp|Thr|Arg 315|Gly|Glu|Arg|Cys|Asn 320|
|Leu|Asp|Asp|Arg|Asp 325|Arg|Ser|Glu|Leu|Ser 330|Pro|Leu|Leu|Leu|Ser 335|Thr|
|Thr|Gln|Trp|Gln 340|Val|Leu|Pro|Cys|Ser 345|Phe|Thr|Thr|Leu|Pro 350|Ala|Leu|
|Thr|Thr|Gly 355|Leu|Ile|His|Leu|His 360|Gln|Asn|Ile|Val|Asp 365|Val|Gln|Tyr|
|Leu|Tyr 370|Gly|Val|Gly|Ser|Ser 375|Ile|Val|Ser|Trp|Ala 380|Ile|Lys|Trp|Glu|
|Tyr 385|Val|Ile|Leu|Leu|Phe 390|Leu|Leu|Leu|Ala|Asp 395|Ala|Arg|Val|Cys|Ser 400|
|Cys|Leu|Trp|

( 2 ) INFORMATION FOR SEQ ID NO:6:

( i ) SEQUENCE CHARACTERISTICS:
        ( A ) LENGTH: 943 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:6:

```
ACAATACGTG TGTCACCCAG ACAGTCGACT TCAGCCTTGA CCCTACCTTC ACCATTGAAA        60
CAACAACGCT TCCCCAGGAT GCTGTCTCCC GCACTCAACG TCGGGGCAGG ACTGGCAGGG       120
GGAAGCCAGG CATTTACAGA TTTGTGGCAC CTGGAGAGCG CCCCTCCGGC ATGTTCGACT       180
CGTCCGTCCT CTGCGAGTGC TATGACGCAG GCTGTGCTTG GTATGAGCTC ACGCCCGCCG       240
AGACCACAGT CAGGCTACGA GCATACATGA ACACCCCGGG ACTTCCCGTG TGCCAAGACC       300
```

-continued

```
ATCTTGAGTT TTGGGAGGGC GTCTTCACGG GTCTCACCCA TATAGACGCC CACTTCCTAT      360

CCCAGACAAA GCAGAGTGGG GAAAACCTTC CTTACCTGGT AGCGTACCAA GCCACCGTGT      420

GCGCTAGGGC CCAAGCCCCT CCCCCGTCGT GGGACCAGAT GTGGAAGTGC TTGATTCGTC      480

TCAAGCCCAC CCTCCATGGG CCAACACCCC TGCTATACCG ACTGGGCGCT GTTCAGAATG      540

AAGTCACCCT GACGCACCCA ATCACCAAAT ATATCATGAC ATGCATGTCG GCTGACCTGG      600

AGGTCGTCAC GAGTACCTGG GTGCTCGTGG GCGGCGTTCT GGCTGCTTTG GCCGCGTATT      660

GCCTATCCAC AGGCTGCGTG GTCATAGTAG GCAGGGTCAT TTTGTCCGGG AAGCCGGCAA      720

TCATACCCGA CAGGGAAGTC CTCTACCGGG AGTTCGATGA GATGGAAGAG TGCTCTCAGC      780

ACTTGCCATA CATCGAGCAA GGGATGATGC TCGCCGAGCA GTTCAAGCAG AAGGCCCTCG      840

GCCTCCTGCA AACACGGTCC CGCCAGGCAG AGGTCATCAC CCCTGCTGTC CAGACCAACT      900

GGCAGAGACT CGAGGCCTTC TGGGCGAAGC ATATGTGGAA CTT                        943
```

( 2 ) INFORMATION FOR SEQ ID NO:7:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Asn Thr Cys Val Thr Gln Thr Val Asp Phe Ser Leu Asp Pro Thr Phe
 1               5                  10                  15

Thr Ile Glu Thr Thr Thr Leu Pro Gln Asp Ala Val Ser Arg Thr Gln
                20                  25                  30

Arg Arg Gly Arg Thr Gly Arg Gly Lys Pro Gly Ile Tyr Arg Phe Val
                35                  40                  45

Ala Pro Gly Glu Arg Pro Ser Gly Met Phe Asp Ser Ser Val Leu Cys
            50              55                  60

Glu Cys Tyr Asp Ala Gly Cys Ala Trp Tyr Glu Leu Thr Pro Ala Glu
 65                 70                  75                  80

Thr Thr Val Arg Leu Arg Ala Tyr Met Asn Thr Pro Gly Leu Pro Val
                85                  90                  95

Cys Gln Asp His Leu Glu Phe Trp Glu Gly Val Phe Thr Gly Leu Thr
                100                 105                 110

His Ile Asp Ala His Phe Leu Ser Gln Thr Lys Gln Ser Gly Glu Asn
            115                 120                 125

Leu Pro Tyr Leu Val Ala Tyr Gln Ala Thr Val Cys Ala Arg Ala Gln
        130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Val Thr Leu Thr His Pro Ile Thr Lys Tyr Ile Met
            180                 185                 190

Thr Cys Met Ser Ala Asp Leu Glu Val Val Thr Ser Thr Trp Val Leu
        195                 200                 205

Val Gly Gly Val Leu Ala Ala Leu Ala Ala Tyr Cys Leu Ser Thr Gly
        210                 215                 220

Cys Val Val Ile Val Gly Arg Val Ile Leu Ser Gly Lys Pro Ala Ile
225                 230                 235                 240

Ile Pro Asp Arg Glu Val Leu Tyr Arg Glu Phe Asp Glu Met Glu Glu
```

|   |   |   |   |   | 245 |   |   |   |   | 250 |   |   |   |   | 255 |   |   |
|---|---|---|---|---|---|---|---|---|---|---|---|---|---|---|---|---|---|
| Cys | Ser | Gln | His | Leu | Pro | Tyr | Ile | Glu | Gln | Gly | Met | Met | Leu | Ala | Glu |
|   |   |   | 260 |   |   |   |   | 265 |   |   |   |   | 270 |   |   |
| Gln | Phe | Lys | Gln | Lys | Ala | Leu | Gly | Leu | Leu | Gln | Thr | Arg | Ser | Arg | Gln |
|   |   | 275 |   |   |   |   | 280 |   |   |   |   | 285 |   |   |   |
| Ala | Glu | Val | Ile | Thr | Pro | Ala | Val | Gln | Thr | Asn | Trp | Gln | Arg | Leu | Glu |
|   | 290 |   |   |   |   | 295 |   |   |   |   | 300 |   |   |   |   |
| Ala | Phe | Trp | Ala | Lys | His | Met | Trp | Asn |
| 305 |   |   |   |   | 310 |   |   |   |

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:8:

ACAATACGTG TGTCACC 17

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:9:

AAGTTCCACA TATGCTTCGC 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:10:

TCCGTTGGCA TAACTGATAG 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:11:

CTATCAGTTA TGCCAACGGA 20

( 2 ) INFORMATION FOR SEQ ID NO:12:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other
 ( A ) DESCRIPTION: DNA primer ( x i ) SEQUENCE DESCRIPTION: SEQ ID NO:12:

GTTGCCCGCC CCTCCGATGT 20

( 2 ) INFORMATION FOR SEQ ID NO:13:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other
 ( A ) DESCRIPTION: DNA primer ( x i ) SEQUENCE DESCRIPTION: SEQ ID NO:13:

CCCAGCCCCG TGGTGGTGGG 20

( 2 ) INFORMATION FOR SEQ ID NO:14:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: Other
 ( A ) DESCRIPTION: DNA primer ( x i ) SEQUENCE DESCRIPTION: SEQ ID NO:14:

CCACAAGCAG GAGCAGACGC 20

( 2 ) INFORMATION FOR SEQ ID NO:15:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: Other
 ( A ) DESCRIPTION: DNA primer ( x i ) SEQUENCE DESCRIPTION: SEQ ID NO:15:

CCATGGCGTT AGTATGAGT 19

( 2 ) INFORMATION FOR SEQ ID NO:16:

( i ) SEQUENCE CHARACTERISTICS:
 ( A ) LENGTH: 18 base pairs
 ( B ) TYPE: nucleic acid
 ( C ) STRANDEDNESS: single
 ( D ) TOPOLOGY: linear ( i i ) MOLECULE TYPE: Other
 ( A ) DESCRIPTION: DNA primer ( x i ) SEQUENCE DESCRIPTION: SEQ ID NO:16:

GCAGGTCTAC GAGACCTC 18

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other
    ( A ) DESCRIPTION: DNA primer ( x i ) SEQUENCE DESCRIPTION: SEQ ID NO:17:

TTCTGGAAGA CGGCGTGAAC  20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:18:

TCATCATATC CCATGCCATG  20

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:19:

CCTTCACCAT TGAGACAATC ACGCTCCCCC AGGATGCTGT  40

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:20:

CTGTCCTGAG AGGCTAGCCA GCTGCCGACC CCTTACCGAT  40

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:21:

AGGTCGGGCG CGCCCACCTA CAGCTGGGGT GAAAATGATA  40

( 2 ) INFORMATION FOR SEQ ID NO:22:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: Other
- ( A ) DESCRIPTION: DNA probe ( x i ) SEQUENCE DESCRIPTION: SEQ ID NO:22:

```
GTGCAGCCTC CAGGACCCCC                                                          20
```

( 2 ) INFORMATION FOR SEQ ID NO:23:

( i ) SEQUENCE CHARACTERISTICS:
- ( A ) LENGTH: 20 base pairs
- ( B ) TYPE: nucleic acid
- ( C ) STRANDEDNESS: single
- ( D ) TOPOLOGY: linear ( i i ) MOLECULE TYPE: Other
- ( A ) DESCRIPTION: DNA probe ( x i ) SEQUENCE DESCRIPTION: SEQ ID NO:23:

```
CTCGTACACA ATACTCGAGT                                                          20
```

( 2 ) INFORMATION FOR SEQ ID NO:24:

( i ) SEQUENCE CHARACTERISTICS:
- ( A ) LENGTH: 256 base pairs
- ( B ) TYPE: nucleic acid
- ( C ) STRANDEDNESS: single
- ( D ) TOPOLOGY: linear ( i i ) MOLECULE TYPE: Other
- ( A ) DESCRIPTION: cDNA to genomic RNA ( x i ) SEQUENCE DESCRIPTION: SEQ ID NO:24:

```
CCATGGCGTT AGTATGAGTG TCGTGCAGCC TCCAGGACCC CCCCTCCCGG GAGAGCCATA              60
GTGGTCTGCG GAACCGGTGA GTACACCGGA ATTGCCAGGA CGACCGGGTC CTTTCTTGGA             120
TAAACCCGCT CAATGCCTGG AGATTTGGGC GCGCCCCGC  GAGACTGCTA GCCGAGTAGT             180
GTTGGGTCGC GAAAGGCCTT GTGGTACTGC CTGATAGGGT GCTTGCGAGT GCCCCGGGAG             240
GTCTCGTAGA CCGTGC                                                             256
```

( 2 ) INFORMATION FOR SEQ ID NO:25:

( i ) SEQUENCE CHARACTERISTICS:
- ( A ) LENGTH: 256 base pairs
- ( B ) TYPE: nucleic acid
- ( C ) STRANDEDNESS: single
- ( D ) TOPOLOGY: linear ( i i ) MOLECULE TYPE: Other
- ( A ) DESCRIPTION: cDNA to genomic RNA ( x i ) SEQUENCE DESCRIPTION: SEQ ID NO:25:

```
CCATGGCGTT AGTATGAGTG TCGTGCAGCC TCCAGGACCC CCCCTCCCGG GAGAGCCATA              60
GTGGTCTGCG GAGCCGGTGA GTACACCGGA ATTGCCAGGA CGACCGGGTC CTTTCTTGGA             120
TAAACCCGCT CAATGCCTGG AGATTTGGGC GCGCCCCGC  AAGACTGCTA GCCGAGTAGT             180
GTTGGGTCGC GAAAGGCCTT GTGGTACTGC CTGATAGGGT GCTTGCGAGT GCCCCGGGAG             240
GTCTCGTAGA CCGTGC                                                             256
```

( 2 ) INFORMATION FOR SEQ ID NO:26:

(i) SEQUENCE CHARACTERISTICS:
   (A) LENGTH: 256 base pairs
   (B) TYPE: nucleic acid
   (C) STRANDEDNESS: single
   (D) TOPOLOGY: linear (ii) MOLECULE TYPE: Other
   (A) DESCRIPTION: cDNA to genomic RNA (xi) SEQUENCE DESCRIPTION: SEQ ID NO:26:

| | | | | | | |
|---|---|---|---|---|---|---|
| CCATGGCGTT | AGTATGAGTG | TCGTGCAGCC | TCCAGGACCC | CCCCTCCCGG | GAGAGCCATA | 60 |
| GTGGTCTGCG | GAACCGGTGA | GTACACCGGA | ATTGCCAGGA | CGACCGGGTC | CTTTCTTGGA | 120 |
| TAAACCCGCT | CAATGCCTGG | AGATTTGGGC | GCGCCCCCGC | GAGACTGCTA | GCCGAGTAGT | 180 |
| GTTGGGTCGC | GAAAGGCCTT | GTGGTACTGC | CTGATAGGGT | GCTTGCGAGT | GCCCCGGGAG | 240 |
| GTCTCGTAGA | CCGTGC | | | | | 256 |

(2) INFORMATION FOR SEQ ID NO:27:

(i) SEQUENCE CHARACTERISTICS:
      (A) LENGTH: 501 base pairs
      (B) TYPE: nucleic acid
      (C) STRANDEDNESS: single
      (D) TOPOLOGY: linear (ii) MOLECULE TYPE: Other
      (A) DESCRIPTION: cDNA to genomic RNA (xi) SEQUENCE DESCRIPTION: SEQ ID NO:27:

| | | | | | | |
|---|---|---|---|---|---|---|
| TTCTGGAAGA | CGGCGTGAAC | TATGCAACAG | GGAACCTTCC | TGGTTGCTCT | TTCTCTATCT | 60 |
| TCCTTCTGGC | CCTGCTCTCT | TGCTTGACTG | TGCCCGCTTC | GGCCTACCAA | GTGCGCAATT | 120 |
| CCACGGGGCT | TTACCACGTC | ACCAATGATT | GCCCTAACTC | GAGTATTGTG | TACGAGGCGG | 180 |
| CCGATGCCAT | CCTGCACACT | CCGGGGTGCG | TCCCTTGCGT | TCGTGAGGGC | AACGCCTCGA | 240 |
| GGTGTTGGGT | GGCGATGACC | CCTACGGTGG | CCACCAGGGA | TGGAAGACTC | CCCGCGACGC | 300 |
| AGCTTCGACG | TCACATCGAT | CTGCTTGTCG | GGAGCGCCAC | CCTCTGTTCG | GCCCTCTACG | 360 |
| TGGGGACCT | ATGCGGGTCT | GTCTTTCTTG | TCGGCCAATT | GTTCACCTTC | TCTCCCAGGC | 420 |
| GCCACTGGAC | GACGCAAGGT | TGCAATTGCT | CTATCTATCC | CGGCCATATA | ACGGGTCACC | 480 |
| GCATGGCATG | GGATATGATG | A | | | | 501 |

(2) INFORMATION FOR SEQ ID NO:28:

(i) SEQUENCE CHARACTERISTICS:
      (A) LENGTH: 501 base pairs
      (B) TYPE: nucleic acid
      (C) STRANDEDNESS: single
      (D) TOPOLOGY: linear (ii) MOLECULE TYPE: Other
      (A) DESCRIPTION: cDNA to genomic RNA (xi) SEQUENCE DESCRIPTION: SEQ ID NO:28:

| | | | | | | |
|---|---|---|---|---|---|---|
| TTCTGGAGGA | CGGCGTGAAC | TATGCAACAG | GGAATTTGCC | CGGTTGCTCT | TTCTCTATCT | 60 |
| TCCTCTTGGC | TCTGCTGTCC | TGTTTGACCA | TCCCAGCTTC | CGCTTATGAA | GTGCGCAACG | 120 |
| TGTCCGGGAT | ATACCATGTC | ACAAACGACT | GCTCCAACTC | AAGCATTGTG | TATGAGGCGG | 180 |
| CGGACGTGAT | CATGCATGCC | CCCGGGTGCG | TGCCCTGCGT | TCGGGAGAAC | AATTCCTCCC | 240 |
| GTTGCTGGGT | AGCGCTCACT | CCCACGCTCG | CGGCCAGGAA | TGCCAGCGTC | CCCACTACGA | 300 |
| CATTACGACG | CCACGTCGAC | TTGCTCGTTG | GGACGGCTGC | TTTCTGCTCC | GCTATGTACG | 360 |

-continued

| TGGGGGATCT | CTGCGGATCT | GTTTTCCTCA | TCTCCCAGCT | GTTCACCTTC | TCGCCTCGCC | 420 |
| GGCATGAGAC | AGTACAGGAC | TGCAACTGCT | CAATCTATCC | CGGCCACGTA | TCAGGCCATC | 480 |
| GCATGGCTTG | GGATATGATG | A | | | | 501 |

( 2 ) INFORMATION FOR SEQ ID NO:29:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:29:

| TTCTGGAAGA | CGGCGTGAAC | TATGCAACAG | GGAACCTTCC | TGGTTGCTCT | TTCTCTATCT | 60 |
| TCCTTCTGGC | CCTGCTCTCT | TGCCTGACTG | TGCCCGCTTC | AGCCTACCAA | GTGCGCAACT | 120 |
| CCACAGGGCT | TTATCATGTC | ACCAATGATT | GCCCTAACTC | GAGTATTGTG | TACGAGGCGC | 180 |
| ACGATGCCAT | CCTGCATACT | CCGGGGTGTG | TCCCTTGCGT | TCGCGAGGGC | AACGTCTCGA | 240 |
| GGTGTTGGGT | GGCGATGACC | CCCACGGTAG | CCACCAGGGA | CGGAAGACTC | CCCGCGACGC | 300 |
| AGCTTCGACG | TCACATCGAT | CTGCTTGTCG | GGAGCGCCAC | CCTCTGTTCG | GCCCTCTACG | 360 |
| TGGGGATCT | GTGCGGGTCC | GTCTTCCTTA | TTGGTCAACT | GTTTACCTTC | TCTCCAGGC | 420 |
| GCCACTGGAC | AACGCAAGGC | TGCAATTGTT | CTATCTACCC | CGGCCATATA | ACGGGTCATC | 480 |
| GCATGGCATG | GGATATGATG | A | | | | 501 |

( 2 ) INFORMATION FOR SEQ ID NO:30:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:30:

| TTCTGGAGGA | CGGCGTGAAC | TATGCAACAG | GGAACTTGCC | CGGTTGCTCT | TTCTCTATCT | 60 |
| TCCTCTTGGC | TTTGCTGTCC | TGTTTGACCA | TCCCAGCTTC | CGCTTATGAA | GTGCGCAACG | 120 |
| TGTCCGGGAT | ATACCATGTC | ACGAACGACT | GCTCCAACTC | AAGCATTGTG | TATGAGGCAG | 180 |
| CGGACATGAT | CATGCATACT | CCCGGGTGCG | TGCCCTGCGT | TCGGGAGGAC | AACAGCTCCC | 240 |
| GTTGCTGGGT | AGCGCTCACT | CCCACGCTCG | CGGCCAGGAA | TGCCAGCGTC | CCCACTACGA | 300 |
| CAATACGACG | CCACGTCGAC | TTGCTCGTTG | GGGCGGCTGC | TTTCTGCTCC | GCTATGTACG | 360 |
| TGGGGGATCT | CTGCGGATCT | GTTTTCCTCG | TCTCCCAGCT | GTTCACCTTC | TCGCCTCGCC | 420 |
| GGCATGAGAC | AGTGCAGGAC | TGCAACTGCT | CAATCTATCC | CGGCCATTTA | TCAGGTCACC | 480 |
| GCATGGCTTG | GGATATGATG | A | | | | 501 |

( 2 ) INFORMATION FOR SEQ ID NO:31:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

| Leu<br>1 | Glu | Asp | Gly | Val<br>5 | Asn | Tyr | Ala | Thr | Gly<br>10 | Asn | Leu | Pro | Gly | Cys<br>15 | Ser |
|---|---|---|---|---|---|---|---|---|---|---|---|---|---|---|---|
| Phe | Ser | Ile | Phe<br>20 | Leu | Leu | Ala | Leu | Leu<br>25 | Ser | Cys | Leu | Thr | Val<br>30 | Pro | Ala |
| Ser | Ala | Tyr<br>35 | Gln | Val | Arg | Asn | Ser<br>40 | Thr | Gly | Leu | Tyr | His<br>45 | Val | Thr | Asn |
| Asp | Cys<br>50 | Pro | Asn | Ser | Ser<br>55 | Ile | Val | Tyr | Glu | Ala<br>60 | Ala | Asp | Ala | Ile | Leu |
| His<br>65 | Thr | Pro | Gly | Cys | Val<br>70 | Pro | Cys | Val | Arg | Glu<br>75 | Gly | Asn | Ala | Ser | Arg<br>80 |
| Cys | Trp | Val | Ala | Met<br>85 | Thr | Pro | Thr | Val | Ala<br>90 | Thr | Arg | Asp | Gly | Arg<br>95 | Leu |
| Pro | Ala | Thr | Gln<br>100 | Leu | Arg | Arg | His | Ile<br>105 | Asp | Leu | Leu | Val | Gly<br>110 | Ser | Ala |
| Thr | Leu | Cys<br>115 | Ser | Ala | Leu | Tyr | Val<br>120 | Gly | Asp | Leu | Cys | Gly<br>125 | Ser | Val | Phe |
| Leu | Val<br>130 | Gly | Gln | Leu | Phe<br>135 | Thr | Phe | Ser | Pro | Arg<br>140 | Arg | His | Trp | Thr | Thr |
| Gln<br>145 | Gly | Cys | Asn | Cys | Ser<br>150 | Ile | Tyr | Pro | Gly | His<br>155 | Ile | Thr | Gly | His | Arg<br>160 |
| Met | Ala | Trp | Asp | Met<br>165 | Met | | | | | | | | | | |

( 2 ) INFORMATION FOR SEQ ID NO:32:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

| Leu<br>1 | Glu | Asp | Gly | Val<br>5 | Asn | Tyr | Ala | Thr | Gly<br>10 | Asn | Leu | Pro | Gly | Cys<br>15 | Ser |
|---|---|---|---|---|---|---|---|---|---|---|---|---|---|---|---|
| Phe | Ser | Ile | Phe<br>20 | Leu | Leu | Ala | Leu | Leu<br>25 | Ser | Cys | Leu | Thr | Ile<br>30 | Pro | Ala |
| Ser | Ala | Tyr<br>35 | Glu | Val | Arg | Asn | Val<br>40 | Ser | Gly | Ile | Tyr | His<br>45 | Val | Thr | Asn |
| Asp | Cys<br>50 | Ser | Asn | Ser | Ser<br>55 | Ile | Val | Tyr | Glu | Ala<br>60 | Ala | Asp | Val | Ile | Met |
| His<br>65 | Ala | Pro | Gly | Cys | Val<br>70 | Pro | Cys | Val | Arg | Glu<br>75 | Asn | Asn | Ser | Ser | Arg<br>80 |
| Cys | Trp | Val | Ala | Leu<br>85 | Thr | Pro | Thr | Leu | Ala<br>90 | Ala | Arg | Asn | Ala | Ser<br>95 | Val |
| Pro | Thr | Thr | Thr<br>100 | Leu | Arg | Arg | His | Val<br>105 | Asp | Leu | Leu | Val | Gly<br>110 | Thr | Ala |
| Ala | Phe | Cys<br>115 | Ser | Ala | Met | Tyr | Val<br>120 | Gly | Asp | Leu | Cys | Gly<br>125 | Ser | Val | Phe |
| Leu | Ile<br>130 | Ser | Gln | Leu | Phe<br>135 | Thr | Phe | Ser | Pro | Arg<br>140 | Arg | His | Glu | Thr | Val |
| Gln<br>145 | Asp | Cys | Asn | Cys | Ser<br>150 | Ile | Tyr | Pro | Gly | His<br>155 | Val | Ser | Gly | His | Arg<br>160 |
| Met | Ala | Trp | Asp | Met<br>165 | Met | | | | | | | | | | |

(2) INFORMATION FOR SEQ ID NO:33:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:33:

```
Leu Glu Asp Gly Val Asn Tyr Ala Thr Gly Asn Leu Pro Gly Cys Ser
 1               5                  10                  15
Phe Ser Ile Phe Leu Leu Ala Leu Leu Ser Cys Leu Thr Val Pro Ala
            20                  25                  30
Ser Ala Tyr Gln Val Arg Asn Ser Thr Gly Leu Tyr His Val Thr Asn
        35                  40                  45
Asp Cys Pro Asn Ser Ser Ile Val Tyr Glu Ala His Asp Ala Ile Leu
    50                  55                  60
His Thr Pro Gly Cys Val Pro Cys Val Arg Glu Gly Asn Val Ser Arg
65                  70                  75                  80
Cys Trp Val Ala Met Thr Pro Thr Val Ala Thr Arg Asp Gly Arg Leu
                85                  90                  95
Pro Ala Thr Gln Leu Arg Arg His Ile Asp Leu Leu Val Gly Ser Ala
            100                 105                 110
Thr Leu Cys Ser Ala Leu Tyr Val Gly Asp Leu Cys Gly Ser Val Phe
            115                 120                 125
Leu Ile Gly Gln Leu Phe Thr Phe Ser Pro Arg Arg His Trp Thr Thr
            130                 135                 140
Gln Gly Cys Asn Cys Ser Ile Tyr Pro Gly His Ile Thr Gly His Arg
145                 150                 155                 160
Met Ala Trp Asp Met Met
                165
```

(2) INFORMATION FOR SEQ ID NO:34:

(i) SEQUENCE CHARACTERISTICS:
        (A) LENGTH: 166 amino acids
        (B) TYPE: amino acid
        (D) TOPOLOGY: linear (ii) MOLECULE TYPE: peptide (xi) SEQUENCE DESCRIPTION: SEQ ID NO:34:

```
Leu Glu Asp Gly Val Asn Tyr Ala Thr Gly Asn Leu Pro Gly Cys Ser
 1               5                  10                  15
Phe Ser Ile Phe Leu Leu Ala Leu Leu Ser Cys Leu Thr Ile Pro Ala
            20                  25                  30
Ser Ala Tyr Glu Val Arg Asn Val Ser Gly Ile Tyr His Val Thr Asn
        35                  40                  45
Asp Cys Ser Asn Ser Ser Ile Val Tyr Glu Ala Ala Asp Met Ile Met
    50                  55                  60
His Thr Pro Gly Cys Val Pro Cys Val Arg Glu Asp Asn Ser Ser Arg
65                  70                  75                  80
Cys Trp Val Ala Leu Thr Pro Thr Leu Ala Ala Arg Asn Ala Ser Val
                85                  90                  95
Pro Thr Thr Thr Ile Arg Arg His Val Asp Leu Leu Val Gly Ala Ala
            100                 105                 110
Ala Phe Cys Ser Ala Met Tyr Val Gly Asp Leu Cys Gly Ser Val Phe
            115                 120                 125
```

|       |       |       |       |       |       |       |       |       |       |       |       |       |       |
|-------|-------|-------|-------|-------|-------|-------|-------|-------|-------|-------|-------|-------|-------|
| Leu   | Val   | Ser   | Gln   | Leu   | Phe   | Thr   | Phe   | Ser   | Pro   | Arg   | Arg   | His   | Glu   | Thr   | Val   |
|       | 130   |       |       |       | 135   |       |       |       |       | 140   |       |       |       |       |       |
| Gln   | Asp   | Cys   | Asn   | Cys   | Ser   | Ile   | Tyr   | Pro   | Gly   | His   | Leu   | Ser   | Gly   | His   | Arg   |
| 145   |       |       |       |       | 150   |       |       |       |       | 155   |       |       |       |       | 160   |
| Met   | Ala   | Trp   | Asp   | Met   | Met   |
|       |       |       |       |       | 165   |

( 2 ) INFORMATION FOR SEQ ID NO:35:

( i ) SEQUENCE CHARACTERISTICS:
        ( A ) LENGTH: 1210 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:35:

| | | | | | |
|---|---|---|---|---|---|
| AATGGCTCAG | CTGCTCCGGA | TCCCACAAGC | CATCTTGGAC | ATGATCGCTG | GTGCTCACTG | 60 |
| GGGAGTCCTG | GCGGGCATAG | CGTATTTCTC | CATGGTGGGG | AACTGGGCGA | AGGTCCTGGT | 120 |
| AGTGCTGCTG | CTATTTGCCG | GCGTCGACGC | GGAAACCCAC | GTCACCGGGG | GAAGTGCCGG | 180 |
| CCACACTGTG | TCTGGATTTG | TTAGCCTCCT | CGCACCAGGC | GCCAAGCAGA | ACGTCCAGCT | 240 |
| GATCAACACC | AACGGCAGTT | GGCACCTCAA | TAGCACGGCT | CTGAACTGCA | ATGATAGCCT | 300 |
| TAACACCGGC | TGGTTGGCAG | GGCTTTTCTA | TCACCACAAG | TTCAACTCTT | CAGGCTGTCC | 360 |
| TGAGAGGCTA | GCCAGCTGCC | GACCCCTTAC | CGATTTTGAC | CAGGGCTGGG | GCCCTATCAG | 420 |
| TTATGCCAAC | GGAAGCGGCC | CCGACCAGCG | CCCCTACTGC | TGGCACTACC | CCCCAAAACC | 480 |
| TTGCGGTATT | GTGCCCGCGA | AGAGTGTGTG | TGGTCCGGTA | TATTGCTTCA | CTCCCAGCCC | 540 |
| CGTGGTGGTG | GGAACGACCG | ACAGGTCGGG | CGCGCCCACC | TACAGCTGGG | GTGAAAATGA | 600 |
| TACGGACGTC | TTCGTCCTTA | ACAATACCAG | GCCACCGCTG | GGCAATTGGT | TCGGTTGTAC | 660 |
| CTGGATGAAC | TCAACTGGAT | TCACCAAAGT | GTGCGGAGCG | CCTCCTTGTG | TCATCGGAGG | 720 |
| GGCGGGCAAC | AACACCCTGC | ACTGCCCCAC | TGATTGCTTC | CGCAAGCATC | CGGACGCCAC | 780 |
| ATACTCTCGG | TGCGGCTCCG | GTCCCTGGAT | CACACCCAGG | TGCCTGGTCG | ACTACCCGTA | 840 |
| TAGGCTTTGG | CATTATCCTT | GTACCATCAA | CTACACCATA | TTTAAAATCA | GGATGTACGT | 900 |
| GGGAGGGGTC | GAACACAGGC | TGGAAGCTGC | CTGCAACTGG | ACGCGGGGCG | AACGTTGCGA | 960 |
| TCTGGAAGAC | AGGGACAGGT | CCGAGCTCAG | CCCGTTACTG | CTGACCACTA | CACAGTGGCA | 1020 |
| GGTCCTCCCG | TGTTCCTTCA | CAACCCTACC | AGCCTTGTCC | ACCGGCCTCA | TCCACCTCCA | 1080 |
| CCAGAACATT | GTGGACGTGC | AGTACTTGTA | CGGGGTGGGG | TCAAGCATCG | CGTCCTGGGC | 1140 |
| CATTAAGTGG | GAGTACGTCG | TTCTCCTGTT | CCTTCTGCTT | GCAGACGCGC | GCGTCTGCTC | 1200 |
| CTGCTTGTGG | | | | | | 1210 |

( 2 ) INFORMATION FOR SEQ ID NO:36:

( i ) SEQUENCE CHARACTERISTICS:
        ( A ) LENGTH: 541 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:36:

-continued

| AATGGCTCAG | CTGCTCCGCA | TCCCACAAGC | CATCTTGGAT | ATGATCGCTG | GTGCTCACTG | 60 |
| GGGAGTCCTG | GCGGGCATAG | CGTATTTCTC | CATGGTGGGG | AACTGGGCGA | AGGTCCTGGT | 120 |
| AGTGCTGTTG | CTGTTTGCCG | GCGTCGACGC | GGAAACCATC | GTCTCCGGGG | GACAAGCCGC | 180 |
| CCGCGCCATG | TCTGGACTTG | TTAGTCTCTT | CACACCAGGC | GCTAAGCAGA | ACATCCAGCT | 240 |
| GATCAACACC | AACGGCAGTT | GGCACATCAA | TAGCACGGCC | TTGAACTGCA | ATGAAAGCCT | 300 |
| TAACACCGGC | TGGTTAGCAG | GGCTTATCTA | TCAACACAAA | TTCAACTCTT | CGGGCTGTCC | 360 |
| CGAGAGGTTG | GCCAGCTGCC | GACGCCTTAC | CGATTTTGAC | CAGGGCTGGG | GCCCTATCAG | 420 |
| TCATGCCAAC | GGAAGCGGCC | CCGACCAACG | CCCCTATTGT | TGGCACTACC | CCCCAAAACC | 480 |
| TTGCGGTATC | GTGCCCGCAA | AGAGCGTATG | TGGCCCGGTA | TATTGCTTCA | CTCCCAGCCC | 540 |
| C | | | | | | 541 |

(2) INFORMATION FOR SEQ ID NO:37:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:37:

| GGTGTCGCAG | TTGCTCCGGA | TCCCACAAGC | TGTCGTGGAC | ATGGTGGCGG | GGGCCCACTG | 60 |
| GGGAGTCCTG | GCGGGCCTTG | CCTACTATTC | CATGGTAGGG | AACTGGGCTA | AGGTCCTGAT | 120 |
| TGTGGCGCTA | CTCTTCGCCG | GCGTTGACGG | GGAGACCTAC | ACGTCGGGGG | GGGCGGCCAG | 180 |
| CCACACCACC | TCCACGCTCG | CGTCCCTCTT | CTCACCTGGG | GCGTCTCAGA | GAATCCAGCT | 240 |
| TGTGAATACC | AACGGCAGCT | GGCACATCAA | CAGGACTGCC | CTAAACTGCA | ATGACTCCCT | 300 |
| CCACACTGGG | TTCCTTGCCG | CGCTGTTCTA | CACACACAGG | TTCAACTCGT | CCGGGTGCCC | 360 |
| GGAGCGCATG | GCCAGCTGCC | GCCCCATTGA | CTGGTTCGCC | CAGGGATGGG | GCCCCATCAC | 420 |
| CTATACTGAG | CCTGACAGCC | CGGATCAGAG | GCCTTATTGC | TGGCATTACG | CGCCTCGACC | 480 |
| GTGTGGTATC | GTACCCGCGT | CGCAGGTGTG | TGGTCCAGTG | TATTGCTTCA | CCCCAAGCCC | 540 |
| T | | | | | | 541 |

(2) INFORMATION FOR SEQ ID NO:38:

(i) SEQUENCE CHARACTERISTICS:
        (A) LENGTH: 325 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:38:

| GGTGTCGCAG | TTACTCCGGA | TCCCACAAGC | TGTCATGGAC | ATGGTGGCGG | GGGCCCACTG | 60 |
| GGGAGTCCTA | GCGGGCCTTG | CCTACTATTC | CATGGTGGGG | AACTGGGCTA | AGGTTTTGAT | 120 |
| TGTGATGCTA | CTCTTTGCCG | GCGTTGACGG | GCATACCCGC | GTGACGGGGG | GGGTGCAAGG | 180 |
| CCACGTCACC | TCTACACTCA | CGTCCCTCTT | TAGACCTGGG | GCGTCCAGA | AAATTCAGCT | 240 |
| TGTAAACACC | AATGGCAGTT | GGCATATCAA | CAGGACTGCC | CTGAACTGCA | ATGACTCCCT | 300 |
| CCAAACTGGG | TTCCTTGCCG | CGCTG | | | | 325 |

( 2 ) INFORMATION FOR SEQ ID NO:39:

( i ) SEQUENCE CHARACTERISTICS:
        ( A ) LENGTH: 403 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

```
Met Ala Gln Leu Leu Arg Ile Pro Gln Ala Ile Leu Asp Met Ile Ala
 1               5                  10                  15

Gly Ala His Trp Gly Val Leu Ala Gly Ile Ala Tyr Phe Ser Met Val
                 20                  25                  30

Gly Asn Trp Ala Lys Val Leu Val Leu Leu Leu Phe Ala Gly Val
             35                  40                  45

Asp Ala Glu Thr His Val Thr Gly Gly Ser Ala Gly His Thr Val Ser
         50                  55                  60

Gly Phe Val Ser Leu Leu Ala Pro Gly Ala Lys Gln Asn Val Gln Leu
 65                  70                  75                  80

Ile Asn Thr Asn Gly Ser Trp His Leu Asn Ser Thr Ala Leu Asn Cys
                 85                  90                  95

Asn Asp Ser Leu Asn Thr Gly Trp Leu Ala Gly Leu Phe Tyr His His
             100                 105                 110

Lys Phe Asn Ser Ser Gly Cys Pro Glu Arg Leu Ala Ser Cys Arg Pro
         115                 120                 125

Leu Thr Asp Phe Asp Gln Gly Trp Gly Pro Ile Ser Tyr Ala Asn Gly
     130                 135                 140

Ser Gly Pro Asp Gln Arg Pro Tyr Cys Trp His Tyr Pro Pro Lys Pro
145                 150                 155                 160

Cys Gly Ile Val Pro Ala Lys Ser Val Cys Gly Pro Val Tyr Cys Phe
                 165                 170                 175

Thr Pro Ser Pro Val Val Val Gly Thr Thr Asp Arg Ser Gly Ala Pro
             180                 185                 190

Thr Tyr Ser Trp Gly Glu Asn Asp Thr Asp Val Phe Val Leu Asn Asn
         195                 200                 205

Thr Arg Pro Pro Leu Gly Asn Trp Phe Gly Cys Thr Trp Met Asn Ser
     210                 215                 220

Thr Gly Phe Thr Lys Val Cys Gly Ala Pro Pro Cys Val Ile Gly Gly
225                 230                 235                 240

Ala Gly Asn Asn Thr Leu His Cys Pro Thr Asp Cys Phe Arg Lys His
                 245                 250                 255

Pro Asp Ala Thr Tyr Ser Arg Cys Gly Ser Gly Pro Trp Ile Thr Pro
             260                 265                 270

Arg Cys Leu Val Asp Tyr Pro Tyr Arg Leu Trp His Tyr Pro Cys Thr
         275                 280                 285

Ile Asn Tyr Thr Ile Phe Lys Ile Arg Met Tyr Val Gly Gly Val Glu
     290                 295                 300

His Arg Leu Glu Ala Ala Cys Asn Trp Thr Arg Gly Glu Arg Cys Asp
305                 310                 315                 320

Leu Glu Asp Arg Asp Arg Ser Glu Leu Ser Pro Leu Leu Leu Thr Thr
                 325                 330                 335

Thr Gln Trp Gln Val Leu Pro Cys Ser Phe Thr Thr Leu Pro Ala Leu
             340                 345                 350

Ser Thr Gly Leu Ile His Leu His Gln Asn Ile Val Asp Val Gln Tyr
         355                 360                 365
```

Leu Tyr Gly Val Gly Ser Ser Ile Ala Ser Trp Ala Ile Lys Trp Glu
              370                 375                 380

Tyr Val Val Leu Leu Phe Leu Leu Leu Ala Asp Ala Arg Val Cys Ser
              385                 390                 395                 400

Cys Leu Trp ( 2 ) INFORMATION FOR SEQ ID NO:40:

( i ) SEQUENCE CHARACTERISTICS:
          ( A ) LENGTH: 180 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:40:

Met Ala Gln Leu Leu Arg Ile Pro Gln Ala Ile Leu Asp Met Ile Ala
              1               5                   10                  15

Gly Ala His Trp Gly Val Leu Ala Gly Ile Ala Tyr Phe Ser Met Val
                              20                  25                  30

Gly Asn Trp Ala Lys Val Leu Val Val Leu Leu Leu Phe Ala Gly Val
                          35                  40                  45

Asp Ala Glu Thr Ile Val Ser Gly Gln Ala Ala Arg Ala Met Ser
              50                      55                  60

Gly Leu Val Ser Leu Phe Thr Pro Gly Ala Lys Gln Asn Ile Gln Leu
              65                  70                  75                  80

Ile Asn Thr Asn Gly Ser Trp His Ile Asn Ser Thr Ala Leu Asn Cys
                                  85                  90                  95

Asn Glu Ser Leu Asn Thr Gly Trp Leu Ala Gly Leu Ile Tyr Gln His
                              100                 105                 110

Lys Phe Asn Ser Ser Gly Cys Pro Glu Arg Leu Ala Ser Cys Arg Arg
                      115                 120                 125

Leu Thr Asp Phe Asp Gln Gly Trp Gly Pro Ile Ser His Ala Asn Gly
                  130                 135                 140

Ser Ala Pro Asp Gln Arg Pro Tyr Cys Trp His Tyr Pro Pro Lys Pro
              145                 150                 155                 160

Cys Gly Ile Val Pro Ala Lys Ser Val Cys Gly Pro Val Tyr Cys Phe
                                  165                 170                 175

Thr Pro Ser Pro
                          180

( 2 ) INFORMATION FOR SEQ ID NO:41:

( i ) SEQUENCE CHARACTERISTICS:
          ( A ) LENGTH: 180 amino acids
          ( B ) TYPE: amino acid
          ( D ) TOPOLOGY: linear ( i i ) MOLECULE TYPE: peptide ( x i ) SEQUENCE DESCRIPTION: SEQ ID NO:41:

Val Ser Gln Leu Leu Arg Ile Pro Gln Ala Val Val Asp Met Val Ala
              1               5                   10                  15

Gly Ala His Trp Gly Val Leu Ala Gly Leu Ala Tyr Tyr Ser Met Val
                              20                  25                  30

Gly Asn Trp Ala Lys Val Leu Ile Val Ala Leu Leu Phe Ala Gly Val
                          35                  40                  45

Asp Gly Glu Thr Tyr Thr Ser Gly Gly Ala Ala Ser His Thr Thr Ser
              50                      55                  60

```
    Thr  Leu  Ala  Ser  Leu  Phe  Ser  Pro  Gly  Ala  Ser  Gln  Arg  Ile  Gln  Leu
    65             70                       75                           80

Val  Asn  Thr  Asn  Gly  Ser  Trp  His  Ile  Asn  Arg  Thr  Ala  Leu  Asn  Cys
                        85                       90                      95

Asn  Asp  Ser  Leu  His  Thr  Gly  Phe  Leu  Ala  Ala  Leu  Phe  Tyr  Thr  His
                   100                      105                      110

Arg  Phe  Asn  Ser  Ser  Gly  Cys  Pro  Glu  Arg  Met  Ala  Ser  Cys  Arg  Pro
              115                      120                      125

Ile  Asp  Trp  Phe  Ala  Gln  Gly  Trp  Gly  Pro  Ile  Thr  Tyr  Thr  Glu  Pro
         130                      135                      140

Asp  Ser  Pro  Asp  Gln  Arg  Pro  Tyr  Cys  Trp  His  Tyr  Ala  Pro  Arg  Pro
    145                      150                      155                      160

Cys  Gly  Ile  Val  Pro  Ala  Ser  Gln  Val  Cys  Gly  Pro  Val  Tyr  Cys  Phe
                        165                      170                      175

Thr  Pro  Ser  Pro
                   180
```

( 2 ) INFORMATION FOR SEQ ID NO:42:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

```
    Val  Ser  Gln  Leu  Leu  Arg  Ile  Pro  Gln  Ala  Val  Met  Asp  Met  Val  Ala
    1              5                        10                           15

Gly  Ala  His  Trp  Gly  Val  Leu  Ala  Gly  Leu  Ala  Tyr  Tyr  Ser  Met  Val
                   20                       25                       30

Gly  Asn  Trp  Ala  Lys  Val  Leu  Ile  Val  Met  Leu  Leu  Phe  Ala  Gly  Val
                   35                       40                       45

Asp  Gly  His  Thr  Arg  Val  Thr  Gly  Gly  Val  Gln  Gly  His  Val  Thr  Ser
         50                       55                       60

Thr  Leu  Thr  Ser  Leu  Phe  Arg  Pro  Gly  Ala  Ser  Gln  Lys  Ile  Gln  Leu
    65             70                       75                           80

Val  Asn  Thr  Asn  Gly  Ser  Trp  His  Ile  Asn  Arg  Thr  Ala  Leu  Asn  Cys
                        85                       90                      95

Asn  Asp  Ser  Leu  Gln  Thr  Gly  Phe  Leu  Ala  Ala  Leu
                   100                      105
```

( 2 ) INFORMATION FOR SEQ ID NO:43:

( i ) SEQUENCE CHARACTERISTICS:
        ( A ) LENGTH: 943 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:43:

```
ACAATACGTG  TGTCACCCAG  ACAGTCGATT  TCAGCCTTGA  CCCTACCTTC  ACCATTGAGA        60

CAATCACGCT  CCCCCAGGAT  GCTGTCTCCC  GCACTCAACG  TCGGGGCAGG  ACTGGCAGGG       120

GGAAGCCAGG  CATCTACAGA  TTTGTGGCAC  CGGGGGAGCG  CCCCTCCGGC  ATGTTCGACT       180

CGTCCGTCCT  CTGTGAGTGC  TATGACGCAG  GCTGTGCTTG  GTATGAGCTC  ACGCCCGCCG       240
```

| | | | | | |
|---|---|---|---|---|---|
|AGACTACAGT|TAGGCTACGA|GCGTACATGA|ACACCCCGGG|GCTTCCCGTG|TGCCAGGACC| 300
|ATCTTGAATT|TTGGGAGGGC|GTCTTTACAG|GCCTCACTCA|TATAGATGCC|CACTTTCTAT| 360
|CCCAGACAAA|GCAGAGTGGG|GAGAACCTTC|CTTACCTGGT|AGCGTACCAA|GCCACCGTGT| 420
|GCGCTAGGGC|TCAAGCCCCT|CCCCCATCGT|GGGACCAGAT|GTGGAAGTGT|TTGATTCGCC| 480
|TCAAGCCCAC|CCTCCATGGG|CCAACACCCC|TGCTATACAG|ACTGGGCGCT|GTTCAGAATG| 540
|AAATCACCCT|GACGCACCCA|GTCACCAAAT|ACATCATGAC|ATGCATGTCG|GCCGACCTGG| 600
|AGGTCGTCAC|GAGCACCTGG|GTGCTCGTTG|GCGGCGTCCT|GGCTGCTTTG|GCCGCGTATT| 660
|GCCTGTCAAC|AGGCTGCGTG|GTCATAGTGG|GCAGGGTCGT|CTTGTCCGGG|AAGCCGGCAA| 720
|TCATACCTGA|CAGGGAAGTC|CTCTACCGAG|AGTTCGATGA|GATGGAAGAG|TGCTCTCAGC| 780
|ACTTACCGTA|CATCGAGCAA|GGGATGATGC|TCGCCGAGCA|GTTCAAGCAG|AAGGCCCTCG| 840
|GCCTCCTGCA|GACCGCGTCC|CGTCAGGCAG|AGGTTATCGC|CCCTGCTGTC|CAGACCAACT| 900
|GGCAAAAACT|CGAGACCTTC|TGGGCGAAGC|ATATGTGGAA|CTT| |943

(2) INFORMATION FOR SEQ ID NO:44:

(i) SEQUENCE CHARACTERISTICS:
        (A) LENGTH: 569 base pairs
        (B) TYPE: nucleic acid
        (C) STRANDEDNESS: single
        (D) TOPOLOGY: linear (ii) MOLECULE TYPE: Other
        (A) DESCRIPTION: cDNA to genomic RNA (xi) SEQUENCE DESCRIPTION: SEQ ID NO:44:

| | | | | | |
|---|---|---|---|---|---|
|GTAACACATG|TGTCACTCAG|ACGGTCGATT|TCAGCTTGGA|TCCCACTCTC|ACCATCGAGA| 60
|CGACGACCGT|GCCCCAAGAT|GCGGTTTCGC|GCACGCAGCG|GCGAGGTAGG|ACTGGCAGGG| 120
|GCAGGAGAGG|CATCTATAGG|TTTGTGACTC|CAGGAGAACG|GCCCTCGGCG|ATGTTCGATT| 180
|CTTCGGTCCT|ATGTGAGTGT|TATGACGCGG|GCTGTGCTTG|GTATGAGCTC|ACGCCCGCTG| 240
|AGACCTCGGT|TAGGTTGCGG|GCTTACCTAA|ATACACCAGG|GTTGCCCGTC|TGCCAGGACC| 300
|ATCTGGAGTT|CTGGGAGAGC|GTCTTCACAG|GCCTCACCCA|CATAGACGCC|CACTTCTTGT| 360
|CCCAGACTAA|GCAGGCAGGA|GACAACTTCC|CCTACCTGGT|AGCATACCAA|GCCACAGTGT| 420
|GCGCCAGGGC|TAAGGCTCCA|CCTCCATCGT|GGGATCAAAT|GTGGAAGTGT|CTCATACGGC| 480
|TAAAGCCTAC|GCTGCACGGG|CCAACGCCCC|TGCTGTATAG|GCTAGGAGCC|GTCCAGAATG| 540
|AGGTCACCCT|CACACACCCT|ATAACCAAA| | | |569

(2) INFORMATION FOR SEQ ID NO:45:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:45:

Asn Thr Cys Val Thr Gln Thr Val Asp Phe Ser Leu Asp Pro Thr Phe
1               5                   10                  15

Thr Ile Glu Thr Ile Thr Leu Pro Gln Asp Ala Val Ser Arg Thr Gln
            20                  25                  30

Arg Arg Gly Arg Thr Gly Arg Gly Lys Pro Gly Ile Tyr Arg Phe Val
        35                  40                  45

Ala Pro Gly Glu Arg Pro Ser Gly Met Phe Asp Ser Ser Val Leu Cys

|  |  |  |  |  | 50 |  |  |  |  | 55 |  |  |  |  | 60 |
|---|---|---|---|---|---|---|---|---|---|---|---|---|---|---|---|

Glu Cys Tyr Asp Ala Gly Cys Ala Trp Tyr Glu Leu Thr Pro Ala Glu
65                  70                  75                  80

Thr Thr Val Arg Leu Arg Ala Tyr Met Asn Thr Pro Gly Leu Pro Val
                85                  90                  95

Cys Gln Asp His Leu Glu Phe Trp Glu Gly Val Phe Thr Gly Leu Thr
            100                 105                 110

His Ile Asp Ala His Phe Leu Ser Gln Thr Lys Gln Ser Gly Glu Asn
            115                 120                 125

Leu Pro Tyr Leu Val Ala Tyr Gln Ala Thr Val Cys Ala Arg Ala Gln
        130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Ile Thr Leu Thr His Pro Val Thr Lys Tyr Ile Met
                180                 185                 190

Thr Cys Met Ser Ala Asp Leu Glu Val Val Thr Ser Thr Trp Val Leu
            195                 200                 205

Val Gly Gly Val Leu Ala Ala Leu Ala Ala Tyr Cys Leu Ser Thr Gly
        210                 215                 220

Cys Val Val Ile Val Gly Arg Val Val Leu Ser Gly Lys Pro Ala Ile
225                 230                 235                 240

Ile Pro Asp Arg Glu Val Leu Tyr Arg Glu Phe Asp Glu Met Glu Glu
                245                 250                 255

Cys Ser Gln His Leu Pro Tyr Ile Glu Gln Gly Met Met Leu Ala Glu
            260                 265                 270

Gln Phe Lys Gln Lys Ala Leu Gly Leu Leu Gln Thr Ala Ser Arg Gln
        275                 280                 285

Ala Glu Val Ile Ala Pro Ala Val Glu Thr Asn Trp Gln Lys Leu Glu
        290                 295                 300

Thr Phe Trp Ala Lys His Met Trp Asn
305                 310

( 2 ) INFORMATION FOR SEQ ID NO:46:

( i ) SEQUENCE CHARACTERISTICS:
        ( A ) LENGTH: 189 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

Asn Thr Cys Val Thr Gln Thr Val Asp Phe Ser Leu Asp Pro Thr Leu
1               5                   10                  15

Thr Ile Glu Thr Thr Thr Val Pro Gln Asp Ala Val Ser Arg Thr Gln
            20                  25                  30

Arg Arg Gly Arg Thr Gly Arg Gly Arg Arg Gly Ile Tyr Arg Phe Val
        35                  40                  45

Thr Pro Gly Glu Arg Pro Ser Ala Met Phe Asp Ser Ser Val Leu Cys
        50                  55                  60

Glu Cys Tyr Asp Ala Gly Cys Ala Trp Tyr Glu Leu Thr Pro Ala Glu
65                  70                  75                  80

Thr Ser Val Arg Leu Arg Ala Tyr Leu Asn Thr Pro Gly Leu Pro Val
                85                  90                  95

| | | | | | | | | | | | | | | |
|---|---|---|---|---|---|---|---|---|---|---|---|---|---|---|
| Cys | Gln | Asp | His 100 | Leu | Glu | Phe | Trp | Glu 105 | Ser | Val | Phe | Thr | Gly 110 | Leu | Thr |
| His | Ile | Asp 115 | Ala | His | Phe | Leu | Ser 120 | Gln | Thr | Lys | Gln | Ala 125 | Gly | Asp | Asn |
| Phe | Pro 130 | Tyr | Leu | Val | Ala | Tyr 135 | Gln | Ala | Thr | Val | Cys 140 | Ala | Arg | Ala | Lys |
| Ala 145 | Pro | Pro | Pro | Ser | Trp 150 | Asp | Gln | Met | Trp | Lys 155 | Cys | Leu | Ile | Arg | Leu 160 |
| Lys | Pro | Thr | Leu | His 165 | Gly | Pro | Thr | Pro | Leu 170 | Leu | Tyr | Arg | Leu | Gly 175 | Ala |
| Val | Gln | Asn | Glu 180 | Val | Thr | Leu | Thr | His 185 | Pro | Ile | Thr | Lys | | | |